United States Patent
Matsui et al.

(10) Patent No.: US 11,448,638 B2
(45) Date of Patent: Sep. 20, 2022

(54) CURRENT MEASUREMENT DEVICE AND CURRENT MEASUREMENT METHOD USING NANOPORE

(71) Applicant: HITACHI HIGH-TECHNOLOGIES CORPORATION, Tokyo (JP)

(72) Inventors: Kazuma Matsui, Tokyo (JP); Yusuke Goto, Tokyo (JP); Rena Akahori, Tokyo (JP); Takahide Yokoi, Tokyo (JP); Michiru Fujioka, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 189 days.

(21) Appl. No.: 16/476,860

(22) PCT Filed: Jan. 10, 2017

(86) PCT No.: PCT/JP2017/000417
§ 371 (c)(1),
(2) Date: Jul. 9, 2019

(87) PCT Pub. No.: WO2018/131064
PCT Pub. Date: Jul. 19, 2018

(65) Prior Publication Data
US 2019/0353636 A1  Nov. 21, 2019

(51) Int. Cl.
*G01N 33/487* (2006.01)
*G01N 27/447* (2006.01)

(52) U.S. Cl.
CPC .  *G01N 33/48721* (2013.01); *G01N 27/44791* (2013.01)

(58) Field of Classification Search
CPC .......... G01N 27/447–44795; G01N 33/48721; B01D 57/00–02; B81B 1/00–008
(Continued)

(56) References Cited

U.S. PATENT DOCUMENTS

| | | |
|---|---|---|
| 8,273,532 B2 | 9/2012 | Gershow et al. |
| 9,777,390 B2 | 10/2017 | Godin et al. |

(Continued)

FOREIGN PATENT DOCUMENTS

| | | |
|---|---|---|
| JP | 2011-501806 A | 1/2011 |
| JP | 2015-108590 A | 6/2015 |

(Continued)

OTHER PUBLICATIONS

Bezrukov, S. M., et al.. Current noise reveals protonation kinetics and number of ionizable sites in an open protein ion channel, Phys. Rev. Lett. 70(15), p. 2352-2355 (1993).

(Continued)

*Primary Examiner* — Bach T Dinh
(74) *Attorney, Agent, or Firm* — Volpe Koenig

(57) ABSTRACT

Provided are a first tank; a second tank; a thin film having a nanopore, which communicates the first tank to the second tank, and disposed between the first and second tanks; a first electrode provided in the first tank; and a second electrode provided in the second tank. A wall surface of the nanopore has an ion adsorption preventing structure to prevent desorption/adsorption of an ion contained in a solution filling the first tank and/or the second tank, and a voltage is applied between the first and second electrodes to measure an ion current flowing through the nanopore.

14 Claims, 26 Drawing Sheets

(58) Field of Classification Search
USPC ............... 204/450–470, 546–550, 600–621, 204/643–645
See application file for complete search history.

(56) References Cited

U.S. PATENT DOCUMENTS

| | | | |
|---|---|---|---|
| 2004/0038260 A1* | 2/2004 | Martin | C12Q 1/6869 435/6.12 |
| 2009/0136958 A1 | 5/2009 | Gershow et al. | |
| 2013/0334048 A1* | 12/2013 | Balagurusamy | G01N 33/48721 204/518 |
| 2015/0108008 A1* | 4/2015 | Kwok | C25F 3/14 205/644 |
| 2015/0109008 A1 | 4/2015 | Godin et al. | |
| 2017/0318966 A1* | 11/2017 | Chen | A47C 1/0307 |
| 2018/0073161 A1* | 3/2018 | Feng | C25F 3/12 |
| 2018/0074006 A1 | 3/2018 | Goto et al. | |

FOREIGN PATENT DOCUMENTS

| | | |
|---|---|---|
| JP | 2015-525114 A | 9/2015 |
| WO | 2016/142925 A1 | 9/2016 |
| WO | 2016/181465 A1 | 11/2016 |

OTHER PUBLICATIONS

Morton, D., et al., Tailored Polymeric Membranes for Mycobacterium Smegmatis Porin A (MspA) Based Biosensors, J Mater Chem B Mater Biol Med. 3(25), p. 5080-5086 (2015).

Tang et al., Surface Modification of Sollid-State Nanopores for Sticky-Free Translocation of Single-Strandid DNA, small, Nov. 12, 2014, vol. 10/No. 21, 4332-4339.

International Search Report dated Apr. 11, 2017 for the PCT International Application No. PCT/JP2017/000417.

* cited by examiner (A)

(B)

(A)

(B)

CURRENT MEASUREMENT DEVICE AND CURRENT MEASUREMENT METHOD USING NANOPORE

TECHNICAL FIELD

The present invention relates to a current measuring apparatus and a current measurement method to measure an ion current when an examinee passes through a nanopore.

BACKGROUND ART

In a field of the next-generation DNA sequencer, a nanopore sequencer draws attention as a method for electrically and directly measuring a DNA base sequence without an elongation reaction or a fluorescence label. The nanopore sequencer determines an ion current flowing through a nanopore embedded in a thin film. When DNA passes through a nanopore, the nanopore is variously plugged depending on bases constituting the DNA, and thus a difference occurs between the current values, making it possible to determine the base sequence.

The nanopore sequence method mainly includes two types depending on nanopore-constituting materials, i.e., a biological nanopore method and a solid-state nanopore method. The biological nanopore method uses a detector including a pore of a modified protein (such as Mycobacterium smegmatis porin A (MspA)) embedded in a lipid bilayer membrane. The solid-state nanopore method uses a detector including a pore processed in an inorganic material. The solid-state nanopore method draws attention as a method that has a less reagent dependence and a smaller number of pretreatment steps than the biological nanopore method, and allows low-cost reading.

CITATION LIST

Nonpatent Literature

Nonpatent Literature 1: Bezrukov, S. M., et al., Current noise reveals protonation kinetics and number of ionizable sites in an open protein ion channel, Phys. Rev. Lett. 70(15), p. 2352-2355 (1993).

Nonpatent Literature 2: Morton, D., et al., Tailored Polymeric Membranes for Mycobacterium Smegmatis Porin A (MspA) Based Biosensors, J Mater Chem B Mater Biol Med. 3(25), p. 5080-5086 (2015).

SUMMARY OF INVENTION

Technical Problem

FIG. 26 shows an ideal current waveform in a nanopore sequence. An ion current during passage of no DNA is referred to as base current. An ion current during passage of DNA is referred to as blockage current. If the base current contains noise, such noise is superimposed on the blockage current. Research and development are therefore underway to reduce noise contained in the base current that has been just measured.

Nonpatent literature 1 describes square-wave noise (hereinafter, referred to as random telegraph noise (RTN)) contained in the base current. FIG. 27 shows experimental results of a base current having RTN. If the base current contains such RTN, RTN as a square-wave noise is superimposed on the blockage current as a square-wave signal, which causes a signal analysis error.

Nonpatent literature 2 describes a method for reducing RTN in the biological nanopore method. RTN is described to be amplified by an interaction of a lipid bilayer membrane and a pore of a modified protein in the biological nanopore method. However, still unclear is a cause of RTN generated in the solid-state nanopore method together with a reduction method of the RTN.

Solution to Problem

A current measuring apparatus of one aspect of the invention includes a first tank, a second tank, a thin film having a nanopore, which communicates the first tank to the second tank, and disposed between the first and second tanks, a first electrode provided in the first tank, and a second electrode provided in the second tank, where a wall surface of the nanopore has an ion adsorption preventing structure to prevent desorption/adsorption of ions contained in a solution filling the first tank and/or the second tank, and a voltage is applied between the first and second electrodes to measure an ion current flowing through the nanopore.

A current measuring method of one aspect of the invention includes the steps of: wetting a wall surface of a nanopore provided in a thin film with a first solution being a solution containing an ion of a group II element or an acidic solution introduced in at least one of the first and second tanks separated by the thin film; and applying a voltage between a first electrode provided in the first tank and a second electrode provided in the second tank to measure an ion current flowing through the nanopore.

Advantageous Effects of Invention

According to the invention, it is possible to reduce RTN in an ion current flowing through a nanopore provided in a thin film of an inorganic material.

Other issues, configurations, and effects are clarified by description of the following embodiment.

DESCRIPTION OF EMBODIMENTS

Figure 1:
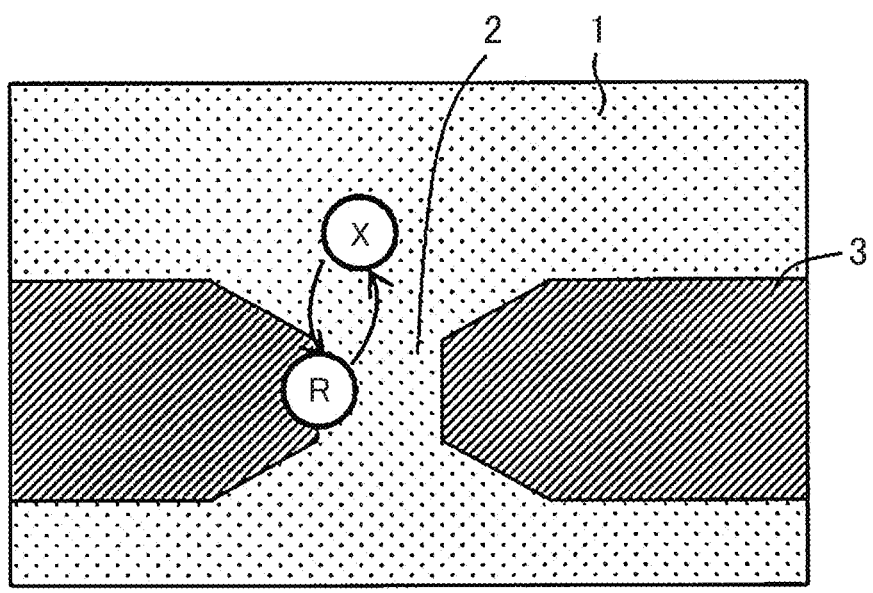
FIG. 1 is a schematic view showing an aspect of RTN generation.

In all drawings for explaining this embodiment, components having the same function are designated by the same numeral, and duplicated description is omitted as much as possible. The invention should not be construed while being limited to the description of the following embodiment. It is easily understood by those skilled in the art that specific configuration of the embodiment can be altered or modified without departing from the idea or the gist of the invention.

In some case, a position, size, a shape, or a range of each of configurations shown in the drawings may not indicate an actual position, size, shape, or range for ease in understanding of the invention. The invention is therefore not necessarily limited to the position, size, shape, or range disclosed in each of the drawings.

The publications and the patent gazettes cited in this specification each directly configure part of the description of the specification.

A component represented in a singular form in this specification should contain a plural form unless specified in the context.

In the following description, "first solution" refers to a solution containing an ion of a group II element or an acidic solution. In addition, "second solution" refers to a solution containing an ion of a group I element, or a solution having a pH higher than that of the first solution when the first solution is an acidic solution having a pH of 5.5 or less. Furthermore, "third solution" refers to a solution different in electrolyte type and concentration from the first solution, and may be a solution equivalent to the second solution.

First, a generation mechanism of RTN is estimated and verified to investigate a solution based on the generation mechanism. RTN is typically considered to be noise due to transition between two or more states, causing two or more discrete current values corresponding to the states. For example, RTN observed in current measurement of a semiconductor device is considered to be generated in the following manner: electron binding or electron dissociation occurs in a film defect formed in an interlayer insulating film, and thus current values are given in correspondence to two states of an electron binding state and an electron dissociation state, resulting in generation of RTN. In the case where the number of the defects is one, transition is typically considered to occur between two levels. However, when the film has a plurality of defects, a large number of pieces of such RTN, which transitions between two levels, are contained and observed as a composite RTN that transitions between a plurality of levels. Inmost reports on nanopore sequencers, RTN generally transitions between a plurality of levels, and thus corresponds to the composite RTN.

Figure 2:
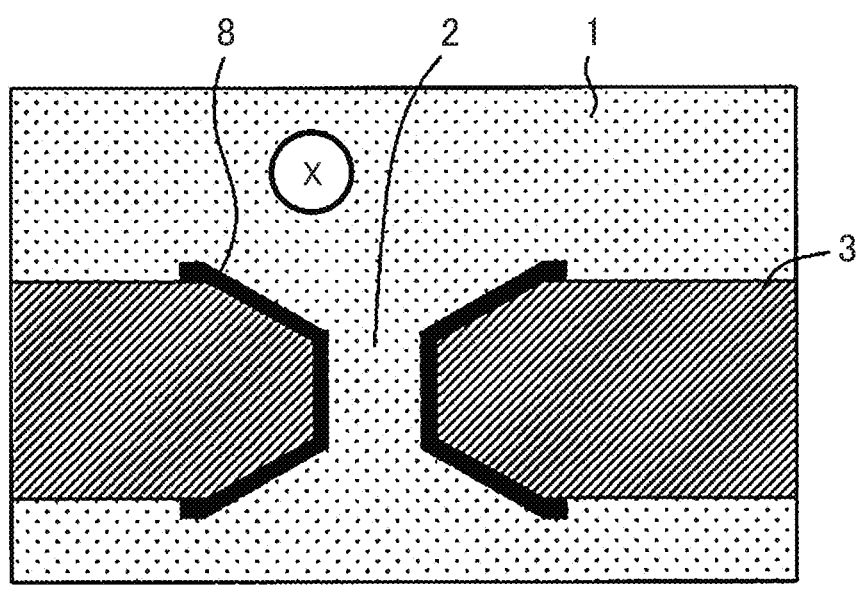
FIG. 2 is a schematic view showing one example where RTN is measured while being reduced.

FIG. 1 is a schematic view showing an aspect of RTN generation. FIG. 2 is a schematic view showing an example where RTN is measured while being reduced. As shown in FIG. 1, we have considered, on a solid-state nanopore (hereinafter, simply referred to as nanopore) 2 formed in a thin film 3, that a similar phenomenon is also found due to binding or dissociation of ions such as a proton, cation, or anion contained in a solution 1 with/from a defect formed during nanopore formation. That is, when an ion to bind or dissociate is represented as X, an ion desorption/adsorption spot to be bound is represented as R, and a state, in which the ion binds to the spot, is represented as RX, a reaction of repeating such binding and dissociation can be represented as follows.

The above-described RTN is generated on a surface on which such a phenomenon occurs. As shown in FIG. 2, therefore, an ion adsorption preventing structure 8 is provided on a wall surface of a thin film having a nanopore 2 and in the vicinity of the wall surface, thereby adsorption of X does not occur and RTN can be suppressed. Such a hypothesis is verified in later description of experimental results.

Figure 3:
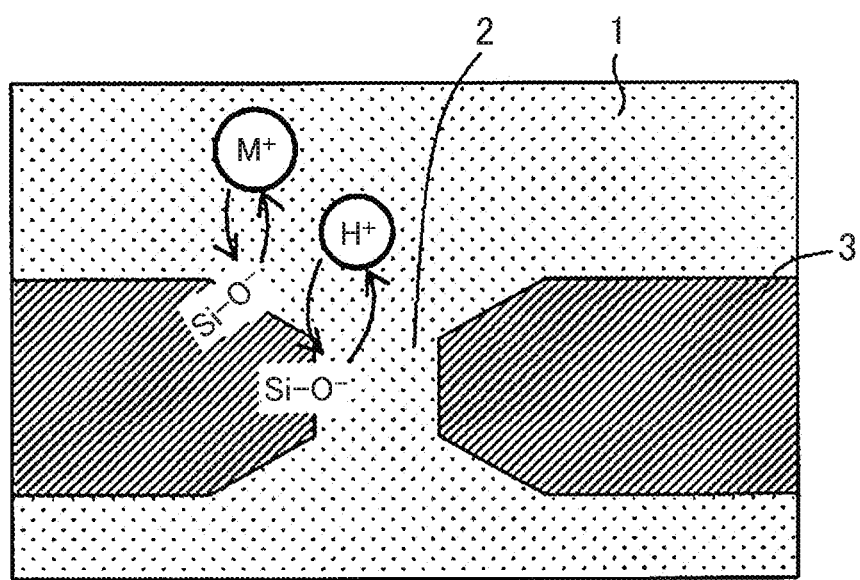
FIG. 3 is a schematic view showing an aspect of RTN generation.

To more specifically describe the reaction spot to/from which the ions such as a proton, cation, or anion binds or dissociates, a SiN film typically used for a nanopore is oxidized at its surface and exposes a silanol group that will act as the reaction spot. As shown in FIG. 3, the following reaction occurs at such a reaction spot.

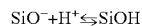

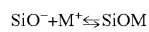

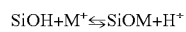

(wherein M represents group I element)

In particular, RTN is generated through repeated desorption and adsorption of a proton (H⁺) and a cation (M⁺) in the solution 1.

Figure 4:
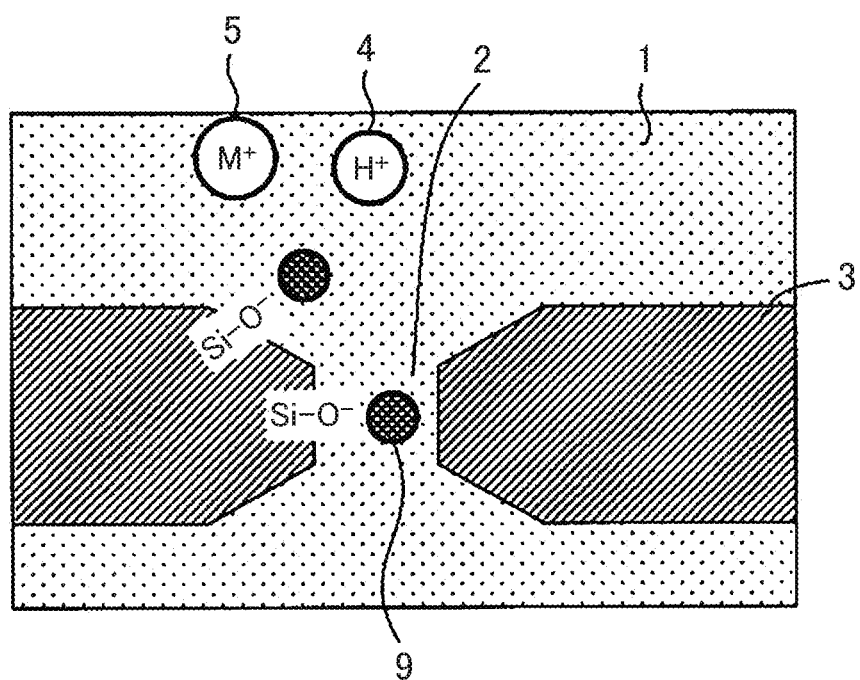
FIG. 4 is a schematic view showing an example where RTN is measured while being reduced.

As shown in FIG. 4, if a cation 9 that tends to adsorb to the silanol group is contained in the solution 1, and once the cation 9 strongly adsorb thereto, since a reaction, such as desorption, adsorption, and exchange of the cation, is suppressed, RTN can be reduced. In this way, an ion, which has a large coefficient of selectivity and is highly adsorbable, is beforehand allowed to adsorb to the reaction-spot, to/from which the ions adsorbs or desorbs, of the nanopore wall surface to prevent desorption/adsorption of another ion. Such a surface structure is referred to as ion adsorption preventing structure.

The order of adsorbability of cations to the silanol group is determined by the selectivity coefficient. In one example, therefore, once the silanol group is wetted by a first solution, i.e., a solution containing an ion ($M^{2+}$) of a group II element or an acidic solution, since $M^{2+}$ or $H^+$ covers the nanopore wall surface and such a cation 9 strongly adsorbs to the wall surface, making it possible to suppress adsorption of other cation species 5 such as $Li^+$, $Na^+$, $K^+$, $Rb^+$, and $Cs^+$ or adsorption of proton 4, and reduce RTN.

The desorption/adsorption of the ions observed as RTN occurs on a nanopore wall surface, at which current concentration occurs, and in the vicinity of the wall surface. Hence, the ion adsorption preventing structure is desirably provided on the nanopore wall surface or in a region at a distance of 100 nm or less from the nanopore. The ion adsorption preventing structure needs to selectively have an anion adsorption preventing structure and/or a cation adsorption preventing structure depending on a material of the thin film and a material of the wall surface forming the nanopore. For example, a surface having an amino group or the like has an anion-exchanging function, and desorbs/adsorbs the anion such as Cl ion or Br ion contained in the solution. On the other hand, a surface having a carboxyl group, a silanol group, or the like has a cation-exchanging function, and desorbs/adsorbs a cation such as Cs ion or Na ion contained in the solution. Furthermore, an element to be a material of the ion adsorption preventing structure needs to be selected according to the selectivity coefficient for each of the anion adsorption preventing structure and the cation adsorption preventing structure. Preferably, a group II element, H, or the like is selected for the cation adsorption preventing structure, and $PO_4$, $SO_4$, $ClO_4$, I, $NO_3$, or the like is selected for the anion adsorption preventing structure.

In many cases, silicon nitride, silicon oxide, hafnium oxide, molybdenum disulfide, or graphene is typically used as a material of the thin film 3 used for the nanopore. Each of such materials contains an oxygen element or has a surface-oxidizable property, and often has a negatively-chargeable surface property (for example, a silanol group in silicon nitride or silicon oxide and a carboxyl group or a hydroxyl group in graphene tend to be negatively charged). Hence, the material often has a cation-absorbable property. Therefore, the cation adsorption preventing structure is typically preferably selected as the ion adsorption preventing structure for the nanopore. The cation adsorption preventing structure may be formed by, for example, a thin film of calcium carbonate, calcium oxide, or calcium silicate, which contains a group II element in the material or surface of the thin film. Alternatively, the structure may be formed by precipitating a compound or the like containing a group II element on the surface of a thin film of SiN or $SiO_2$, or by chemically modifying calcium carbonate or the like by mineralization.

In a more preferable method for forming the cation adsorption preventing structure, as shown in FIG. 4, a wall surface having the nanopore is wetted by a first solution containing an adsorbable cation 9. This method can easily change the surface structure of the nanopore wall surface. In addition, the method makes it possible to suppress RTN without significantly changing the thickness or diameter of the nanopore, and can be used without changing sensor characteristics such as base resolution during measurement of a biopolymer such as DNA as an examinee.

Figure 5:
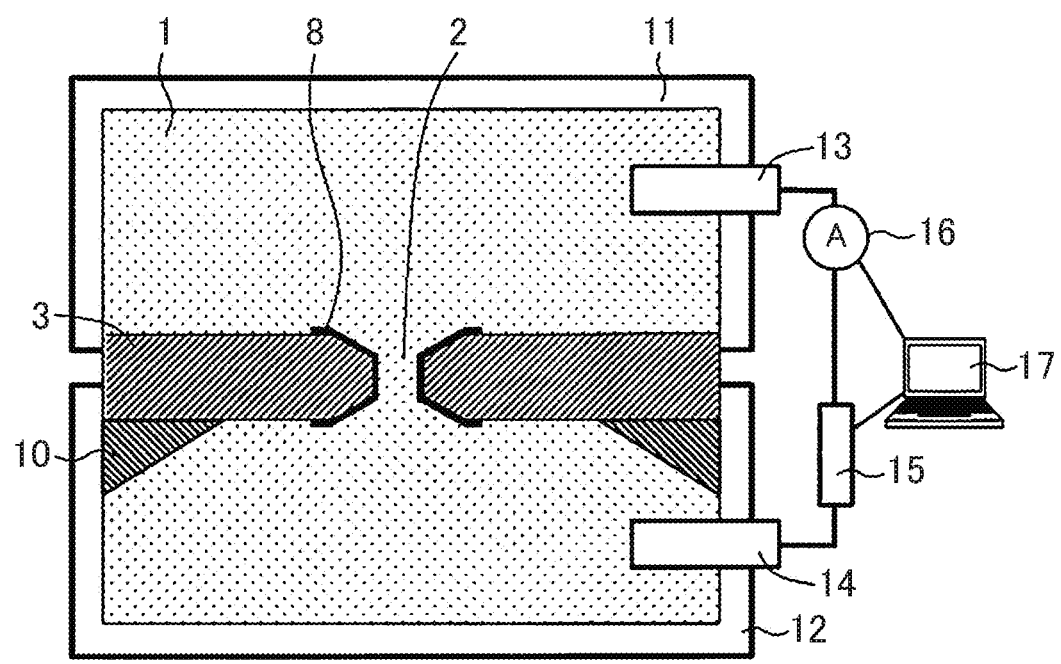
FIG. 5 is a schematic sectional view showing an exemplary configuration of a current measuring apparatus.

A procedure used in this example to measure RTN while suppressing the RTN is now described in detail. FIG. 5 is a schematic sectional view showing an exemplary configuration of a current measuring apparatus of this example, showing an aspect of measuring a current while covering, with the ion adsorption preventing structure 8, a wall surface having the nanopore 2 of the thin film 3 and the vicinity of the wall surface.

The thin film 3 having the nanopore 2 is wetted by the solution 1 while its first surface is disposed in a first tank 11 and a second surface is disposed in a second tank 12. The first tank 11 and the second tank 12 are separated by the thin film 3 and in communication with each other through the nanopore 2. The first tank 11 and the second tank 12 are each filled with the solution 1 containing an electrolyte, a first electrode 13 and a second electrode 14 are provided in the first tank 11 and the second tank 12, respectively, and the first electrode 13 is wetted by the solution in the first tank 11, and the second electrode 14 is wetted by the solution in the second tank 12. A voltage is applied by a power unit 15 between the first electrode 13 and the second electrode 14, thereby a current flowing through the nanopore 2 can be measured by an ammeter 16.

The electrode such as the first electrode 13 or the second electrode 14 is preferably made of a material capable of performing an electron transfer reaction (faradaic reaction) with the electrolyte in the solution 1, and is typically made of silver halide or alkali silver halide. Silver/silver-silver chloride is preferably used as the electrode in light of potential stability and reliability. Each electrode may be made of a material forming a polarized electrode, for example, gold or platinum. In such a case, a substance that can assist the electron transfer reaction, for example, potassium ferricyanide or potassium ferrocyanide is preferably added to the solution in order to secure a stable ion current. Alternatively, a substance capable of performing the electron transfer reaction, for example, one of ferrocenes, is preferably immobilized on the surface of the polarized electrode.

The electrode may be structured such that the entire electrode is made of the above-described material, or the material covers the surface of a base material such as copper or aluminum. The electrode preferably, but not limitedly, has a shape that provides a large area of the surface to be wetted by the solution. The electrode is bonded to a wiring such that an electric signal is sent to a measurement circuit. The power unit 15 may be connected to a personal computer 17 such that an applied voltage can be controlled. The ammeter 16 may also be connected to an apparatus such as a personal computer to configure a measuring system that stores the measured current as data. The ammeter 16 may have an amplifier, which amplifies a current flowing between the electrodes upon voltage application, and an analog to digital converter (ADC).

The nanopore 2 in this example is provided in the thin film 3 of an inorganic material. The inorganic material may be any material that can be formed by a semiconductor microfabrication technique, and typically includes silicon nitride, silicon oxide, hafnium oxide, molybdenum disulfate, and graphene, preferably silicon nitride or silicon oxide being a Si compound that can be mass-produced by a semiconductor process. However, since RTN caused by adsorption/desorption of the ions is also generated even for a film of graphene or the like, which allows a high base resolution in DNA measurement, this example can be applied to a film of such a two-dimensional material. For example, a device, in which a SiN thin film having a thickness of 1 μm or less and an area of 100 μm² or less is supported by a silicon support substrate of 725 μm thick, is used as a structure 10 supporting the thin film 3.

The nanopore 2 provided in the thin film 3 may be formed by a semiconductor process so as to allow mass production, or by an electron beam of TEM so as to have a small pore size. More preferably, the nanopore 2 is formed by dielectric breakdown induced by applying a high voltage to the thin film 3 and used so as to allow the nanopore 2 having a small pore size to be formed accurately, quickly, and inexpensively.

The RTN treated in this example is generated by desorption/adsorption of a cation having an atomic radius of 1 nm or less. The RTN is therefore a phenomenon notably found during measurement of a current flowing through the nanopore 2 having a relatively small size, of about 100 times or less the size of the cation. Hence, the RTN reduction effect is particularly exhibited when the nanopore 2 has a diameter of 0.1 nm (design limit) to 100 nm and a length of 0.1 nm (design limit) to 100 nm. The RTN reduction effect is more notably exhibited when the nanopore 2 has a diameter of 0.1 nm (design limit) to 10 nm and a length of 0.1 nm (design limit) to 50 nm. The RTN reduction effect is further notably exhibited when the nanopore 2 has a diameter of 0.1 nm (design limit) to 5 nm and a length of 0.1 nm (design limit) to 20 nm. For example, when the nanopore 2 has a diameter of 0.1 nm (design limit) to 5 nm and a length of 0.1 nm (design limit) to 20 nm, and if a current is measured without using the RTN suppression procedure of this example, a variation of 1 nA occurs in a base current of 1 nA due to RTN as shown in experimental results as described later (FIG. 15), which extremely reduces measurement accuracy, and thus makes it extremely difficult to use the nanopore as a sensor. The present method is therefore particularly effectively applied to a relatively small nanopore having a diameter of 0.1 nm (design limit) to 100 nm and a length of 0.1 nm (design limit) to 100 nm.

The diameter of the nanopore is preferably more strictly determined depending on measurement contents. For example, when a biopolymer or bead having a diameter of about 10 nm is analyzed, the nanopore is 100 nm or less, preferably 50 nm or less, and is specifically about 0.9 to 10 nm. For example, a nanopore used for analysis of ssDNA (single-stranded DNA) having a diameter of about 1.4 nm has a diameter of preferably about 1.4 to 10 nm, and more preferably about 1.4 to 2.5 nm. In addition, for example, a nanopore used for analysis of dsDNA (double-stranded DNA) having a diameter of about 2.6 nm has a diameter of preferably about 3 to 10 nm, and more preferably about 3 to 5 nm.

The thickness of the nanopore is also preferably more strictly determined depending on measurement contents, and is preferably 0.1 to 200 nm, and more preferably 0.1 to 100 nm. When a biopolymer or the like is analyzed as an examinee, the thickness is adjusted to two times or more, preferably three times or more, and more preferably five times or more of a monomer unit configuring the biopolymer. For example, when the biopolymer is composed of nucleic acid, the thickness is preferably adjusted to at least a size of three bases, for example, about 1 nm or more. In light of resolution of a nanopore sensor, thickness of the nanopore is preferably small in order to understand a shape or a constituent (for DNA, a base type or the like) of a biopolymer. For example, the thickness of the nanopore is preferably adjusted to 200 nm or less, more preferably 100 nm or less in order to measure a streptococcus having a biopolymer size of about 1 to 10 μm and understand a straight-chain shape. Furthermore, since an interval between bases is short, about 0.5 nm, the thickness of the nanopore is preferably 30 nm or less, and more preferably 10 nm or less in order to analyze abase species of DNA as a biopolymer composed of nucleic acids. This makes it possible to analyze the shape or the constituent of the biopolymer at high resolution. The shape of the nanopore is basically a circular shape, but may be an ellipsoidal or polygonal shape.

Figure 6:
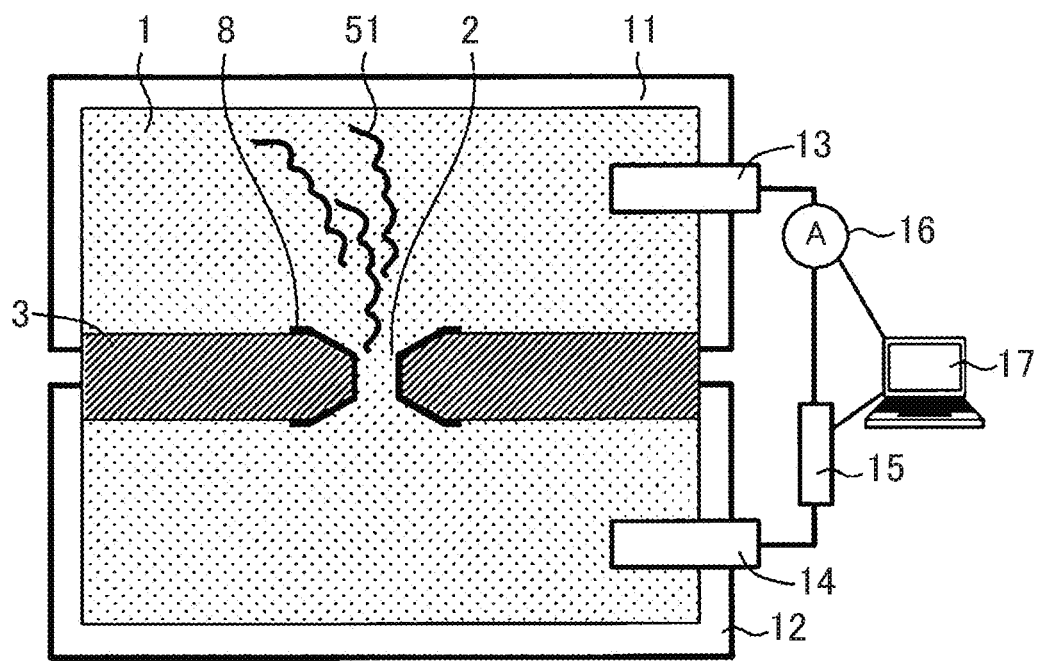
FIG. 6 is a schematic sectional view showing an exemplary measurement using the current measuring apparatus.

In an exemplary measurement using the current measuring apparatus of this example, an ion species contained in the solution is identified from a value of a current flowing through the nanopore 2. Suppressing RTN by this method makes it possible to improve measurement accuracy. FIG. 6 is a schematic sectional view showing an exemplary measurement using the measuring apparatus of this example. In the exemplary measurement shown in FIG. 6, a biopolymer 51 such as DNA is passed through the nanopore 2 to measure a blockage current.

In such measurement, if a measurement signal contains RTN, since a variation due to RTN is not distinguishable from a variation due to the blockage current, the RTN reduction effect is exhibited particularly in measurement of the blockage current. The biopolymer 51 to be analyzed may be any object, of which the electrical characteristics, particularly the resistance value, vary when the object passes through the nanopore 2, and is composed of a nucleic acid. Specifically, the biopolymer 51 includes RNA (single-stranded RNA or double-stranded RNA), DNA (single-stranded DNA or double-stranded DNA), PNA (peptide nucleic acid), oligonucleotide, aptamer, and combinations of them (for example, hybrid nucleic acid).

The biopolymer 51 may exist in a living body, or may be induced from a substance in a living body. For example, the biopolymer 51 includes a polymer containing a sequence or a constituent that does not exist in nature, for example, a sequence such as poly (A) or poly (T), an artificially synthesized polymer molecule, a nucleic acid prepared by a nucleic-acid amplifying technique such as PCR, and a nucleic acid cloned in a vector. A preparation method of each of such biopolymers is known in the relevant technical filed, and can be appropriately selected by those skilled in the art depending on a type of the biopolymer. In this example, analysis of a biopolymer means property analysis of a nucleic acid constituting the biopolymer. For example, the analysis means analysis of sequence order (sequencing) of monomers of a nucleic acid constituting the biopolymer, determination of length of the nucleic acid, detection of single nucleotide polymorphism, determination of the number of biopolymers, and detection of structural variants (such as copy number variants, insertion, and deletion) in a biopolymer.

There are a plurality of procedures for providing the ion adsorption preventing structure in the nanopore of the thin film to measure a current. In a possible exemplary procedure, the ion adsorption preventing structure is provided, and then a solution is poured into above and below the thin film and a current is measured. In another possible procedure, a nanopore is provided in a thin film by a semiconductor process or the like, and then the ion adsorption preventing structure is provided by surface modification using a chemical reaction or the like in a liquid phase, and a current is measured. In a further possible procedure, a solution is poured into above and below the thin film, and then a nanopore is opened by dielectric breakdown, and then the ion adsorption preventing structure is provided by surface modification using a chemical reaction or the like in a liquid phase, and a current is measured.

In a more preferable method for forming the cation adsorption preventing structure, a wall surface having a nanopore is wetted by a first solution being a solution containing an ion of a group II element or an acidic solution as shown in FIG. 4. This method makes it possible to easily change a surface structure of a nanopore wall surface to form the cation adsorption preventing structure. In addition, this method can suppress RTN without significantly change the thickness or pore size of the nanopore, and can be used without changing sensor characteristics such as base resolution during measurement of a biopolymer such as DNA.

Figure 7:
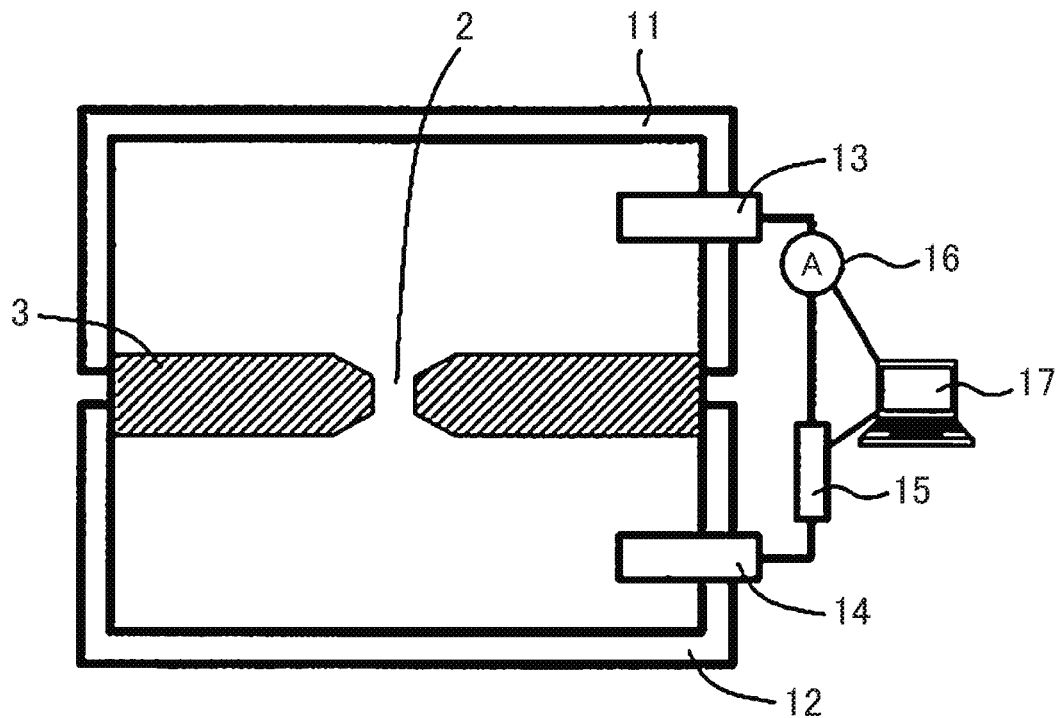
FIG. 7 is a schematic sectional view showing an exemplary procedure for forming an ion adsorption preventing structure by wetting.
Figure 7:
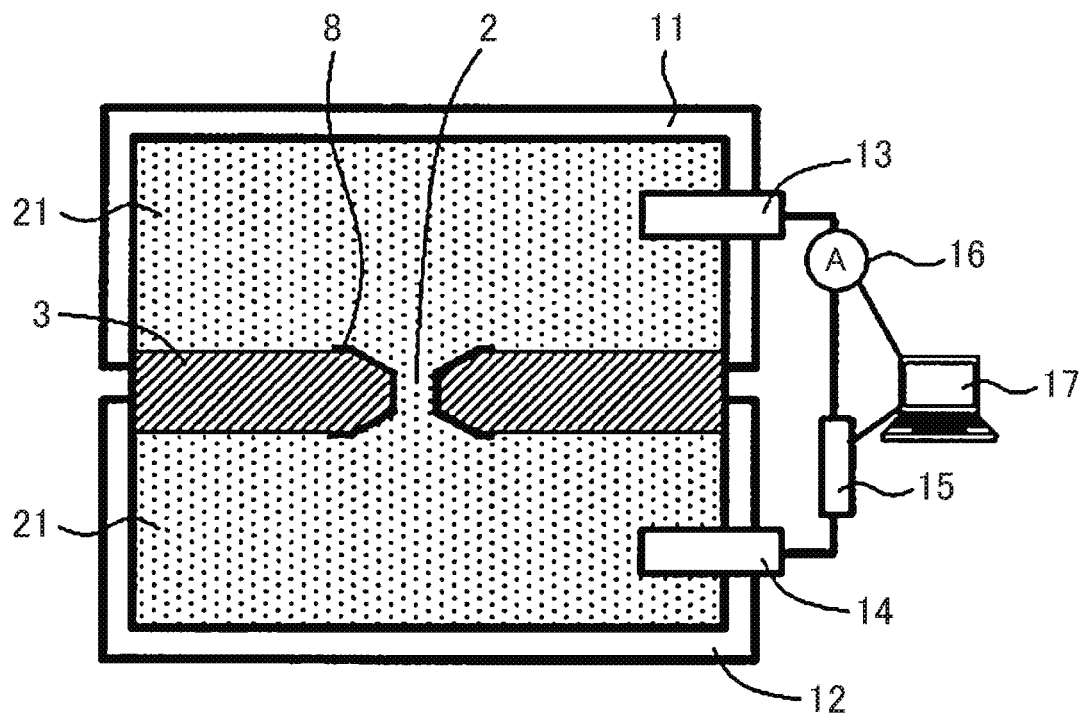

FIG. 7 is a schematic sectional view showing an exemplary procedure for forming an ion adsorption preventing structure on a nanopore wall surface by wetting. First, the nanopore 2 is provided in the thin film 3 by a semiconductor process or the like, and then, as shown in FIG. 7(A), a measuring apparatus is assembled using the thin film 3. Subsequently, as shown in FIG. 7(B), a first solution 21 being a solution containing an ion of a group II element or an acidic solution is introduced into the first tank 11 and the second tank 12 of the measuring apparatus, and the surface of the thin film 3 and the wall surface of the nanopore 2 are wetted by the first solution 21 to form the ion adsorption preventing structure 8, and then, for example, a specimen may be injected into the first tank 11 so that an ion current flowing through the nanopore 2 is measured. When a surface state is thus changed by wetting, it is possible to significantly change the surface state of the film by applying power to the film surface and thus efficiently form the ion adsorption preventing structure 8. Hence, a voltage of 0.1 V or more is desirably applied to the film for 1 sec or more after wetting.

Figure 8:
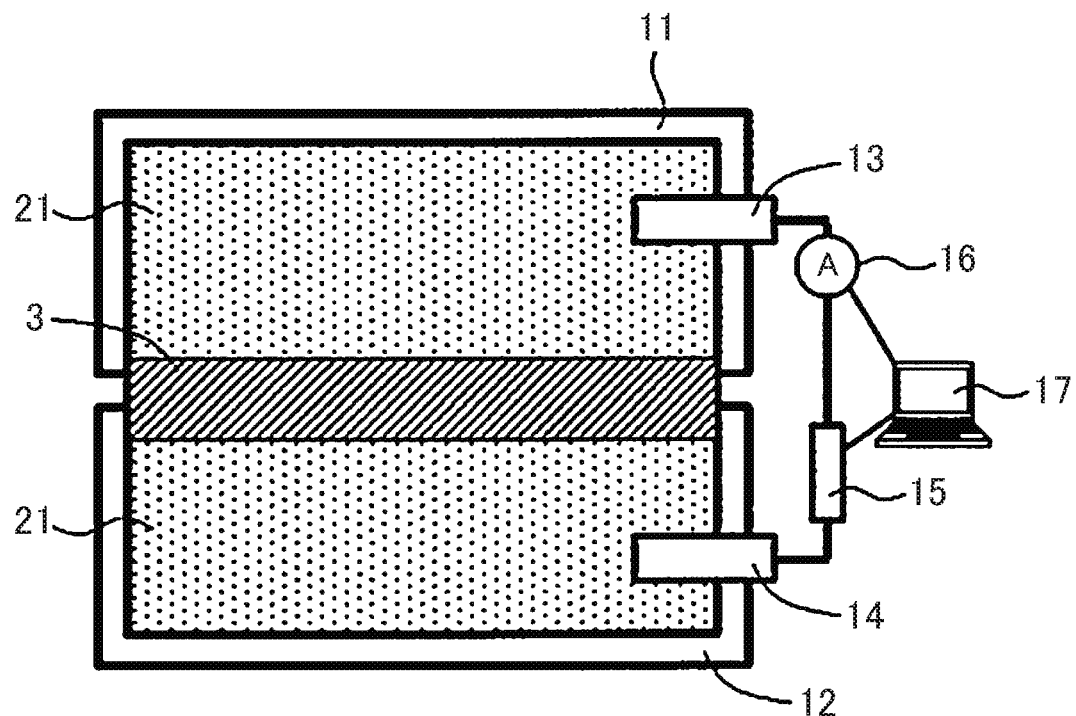
FIG. 8 is a schematic sectional view showing another exemplary procedure for forming the ion adsorption preventing structure.
Figure 8:
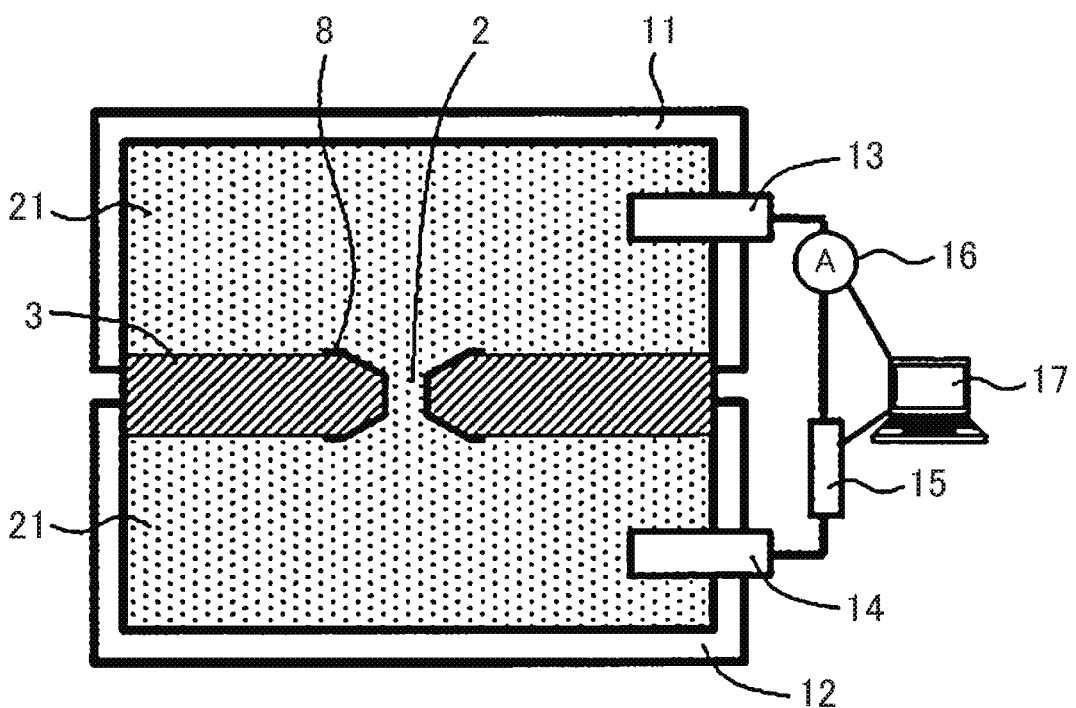

A more preferable method for forming the cation adsorption preventing structure on the nanopore wall surface to perform current measurement is a combination of the method for changing the surface state of the wall surface by wetting and the method for opening the nanopore by dielectric breakdown. FIG. 8 is a schematic sectional view explaining such a current measuring method. In an exemplary specific measuring procedure, as shown in FIG. 8(A), the first solution 21 is poured to fill the first tank 11 and the second tank 12 on both sides of the thin film 3, and then, as shown in FIG. 8(B), a potential difference of 1 V or more is applied between the first electrode 13 and the second electrode 14 to open the nanopore 2 in the thin film 3 by dielectric breakdown, and then an ion current flowing through the nanopore 2 is measured. A higher voltage is thus given through dielectric breakdown. The surface state of the film therefore can be changed and maintained for a long time. In addition, it is possible to concurrently perform opening of the nanopore 2 and formation of the cation adsorption preventing structure 8. It is therefore possible to more easily produce a thin film having the nanopore 2 and the cation adsorption preventing structure 8.

When the above-described procedure is used to apply power to the thin film by voltage application so that the surface state is changed to form the ion adsorption preventing structure, a direction of the voltage applied during changing of the surface state is desirably adjusted to correspond to the direction of the voltage during measurement of the ion current flowing through the nanopore. Specifically, for example, when a positive voltage $+V_1$ [V] is applied to the first electrode 13 to apply power to the film surface while the second electrode 14 has a reference potential, 0 V, in FIG. 7(B), a positive voltage $+V_2$ [V] is desired to be also applied to the first electrode 13 during measurement of the ion current flowing through the nanopore 2 to measure the ion current.

Similarly, when a nanopore is opened in the thin film by dielectric breakdown as in FIG. 8(B), i.e., when a positive voltage $+V_1$ [V] is applied to the first electrode 13 to open the nanopore in the thin film by dielectric breakdown while the second electrode 14 has a reference potential, 0 V, a positive voltage $+V_2$ [V] is desired to be also applied to the first electrode 13 during measurement of the ion current flowing through the nanopore 2 to measure the ion current.

The voltage direction may be reversed so that the first electrode 13 has a negative voltage. For example, when a negative voltage $-V_1$ [V] is applied to the first electrode 13 to apply power to the film surface while the second electrode 14 has a reference potential, 0 V, in FIG. 7(B), a negative voltage $-V_2$ [V] is desired to be also applied to the first electrode 13 during measurement of the ion current flowing through the nanopore 2 to measure the ion current.

As described above, the direction of the voltage applied during changing of the surface state, i.e., during formation of the ion adsorption preventing structure is adjusted to correspond to the direction of the voltage during measurement of the ion current flowing through the nanopore 2. The reason for this is described in the following. For example, a $CaCl_2$ solution containing a group II element is used as the first solution 21, and when a positive voltage $+V_1$ [V] is applied to the first electrode 13 to apply power to the film surface while the second electrode 14 has a reference potential, 0 V, in FIG. 7(B), positively charged $Ca^{2+}$ ions that are ionized in the solution are attracted to a second electrode 14 side. Hence, a reaction more easily proceeds on an upper side of the thin film 3 shown in FIG. 7(B), and robustness of the ion adsorption preventing structure 8 is improved on the upper side of the thin film 3 compared with the lower side thereof.

Subsequently, when the negative voltage $-V_2$ [V] is assumed to be applied to the first electrode 13 during measurement of the ion current flowing through the nanopore 2, a $Ca^{2+}$ ion that has adsorbed to the upper side of the thin film 3 is attracted to the first electrode 13 and thus desorbs, thereby the ion adsorption preventing structure 8 is lost and RTN is easily generated. In addition, when the negative voltage $-V_2$ [V] is applied to the first electrode 13, while cations contained in the solution are strongly attracted to the first electrode 13 side on the lower side of the thin film 3, since robustness of the cation adsorption preventing structure 8 is lower on the lower side than on the upper side of the thin film 3, RTN is easily generated. In the above-described example, therefore, the positive voltage $+V_2$ [V] is preferably applied to the first electrode 13 during measurement of the ion current flowing through the nanopore 2.

A candidate of the first solution 21 includes a solution containing a group II element such as Mg, Ca, Sr, or Ba, and an acidic solution. The group II element in the former or a proton in the latter is allowed to adsorb to the surface of the nanopore 2. The anion contained in the first solution 21 may include ionizable anions, and is preferably selected depending on compatibility with the material of the electrode. For example, when silver halide is used as the electrode material, an ion of a halide of I, Br, or Cl is preferably used as the anion. The anion may be one of organic anions typified by a glutamic acid ion.

When a cation is allowed to adsorb, a cation typically having a large selectivity coefficient for a cation-exchange resin or the like is desirably used, for example, a group II ion is preferably used. Of these, when Ca, Sr, or Ba is selected as a cation having a large selectivity coefficient, since such a cation is more adsorbable to the film surface, RTN can be more reduced. When such a group II cation is contained in the solution, concentration of the cation is desirably high. The RTN reduction effect is known to be given at the lower limit of the concentration of 10 mM, and thus the concentration is desirably 10 mM or more and equal to or less than the saturation concentration.

When a proton is allowed to adsorb, an acidic solution having a pH of 5.5 or less is preferably used to increase the RTN reduction effect, and is more preferably adjusted to a lower PH, such as pH 1. That is, the concentration of [$H^+$] contained in the first solution 21 is preferably $10^{-5.5}$ M or more and equal to or less than the saturation concentration. The solution may be an acidic solution containing a group II element, or a solution containing neither alkali metal element nor group II element, such as HCl.

On the other hand, when the first solution 21 is used to reduce RTN and measure a biopolymer such as DNA, it is known that if a group II element is contained in the solution, the element strongly interacts with the biopolymer such as DNA and a Tm value greatly varies. This may cause formation of a conformation, which varies a behavior of a biopolymer of DNA or the like passing through the nanopore, or prevents the biopolymer from passing through the nanopore. In addition, the acidic solution having a low pH is known to induce a depurination of DNA or the like, which prevents the DNA from maintaining its original structure.

Hence, after the nanopore wall surface is wetted by the first solution, a second solution containing an ion of a group I element is desirably introduced into the first solution to reduce the concentration of the first solution. Even if the second solution is thus additionally introduced, since the group I element has a small selectivity coefficient, the cation adsorption preventing structure is maintained and prevents adsorption of the group I element, so that the RTN suppression state can be maintained. The alternative cation of the group I element contained in the second solution may include any of organic cations composed of organic matters, for example, an ionizable cation typified by an ammonium ion.

When the first solution is an acidic solution having a pH of 5.5 or less, the second solution needs to have a high pH compared with the first solution, and preferably has a pH of 5.5 or more. The upper limit of the pH value is determined as follows. The upper limit of the pH value of a measurement solution is determined by a limit of tolerance of a device and by a limit of tolerance of a biopolymer to be measured. A silicon wafer typically used for a semiconductor nanopore is used as a substrate, and a limit of tolerance of the device is around pH 14 at which silicon etching starts. Such an etching rate is previously known (Lloyd D. Clark, et al. Cesium Hydroxide (CsOH): A Useful Etchant for Micromachining Silicon, Technical Digest, Solid-State Sensor and Actuator Workshop, IEEE, 1988). Although silicon nitride, which is often used as a thin-film material, is not etched even at a pH in a high alkali region, since silicon or silicon oxide as a base is gradually etched in such a pH region, 14 is preferably set as the upper limit of pH. That is, the concentration of [$H^+$] contained in the second solution is preferably $10^{-14}$ to $10^{-5.5}$ M. For another semiconductor material, the [$H^+$] concentration is similarly determined by the device tolerance limit of that material.

On the other hand, it has been found that a long chain of a biopolymer (particularly, DNA) is broken when the solution contains sodium hydroxide (NaOH) of 0.3 M or more. Similar results are obtained for a hydroxide solution that has a different cation species and is known to have a concentration dependence. In the case of DNA as the biopolymer, pH 12 or less is desirable. In a possible phenomenon, when the measurement solution is continuously in contact with the air, pH of the solution gradually shifts to an acidic side through a reaction of the solution with carbon dioxide in the air. To reduce influence of the carbon dioxide, the pH of the solution may be set to a higher alkali side in an initial stage, or concentration of a pH adjuster may be set to be high. A higher concentration of the pH adjuster is more preferable, and the concentration is preferably 50 mM or more and more preferably 100 mM or more.

For example, when water is used as a solvent, electric conductivity of a 1 mol/kg alkali chloride solution at 25° C. is known to be 7.188 $Sm^{-1}$ for LiCl, 8.405 $Sm^{-1}$ for NaCl, 10.84 $Sm^{-1}$ for KCl, 11.04 $Sm^{-1}$ for RbCl, and 10.86 $Sm^{-1}$ for CsCl. Hence, a type of the group I element contained in the second solution is preferably K, Rb, or Cs having a high electric conductivity, and is more preferably Cs that has a largest solubility in water and thus can amplify the electric conductivity by increasing the concentration of Cs. On the other hand, a tradeoff has been concerned. That is, among the group I elements, K, Rb, and Cs (particularly Cs) each have a large coefficient of selectivity, and thus tend to amplify RTN. However, amplification of a signal level during biopolymer analysis and a reduction in RTN can be achieved together through a procedure of replacing the first solution with the second solution containing Cs.

For the ion concentration, the lower limit of the electrolyte concentration is preferably provided in light of a signal-to-noise ratio. Venta, K., et al., Differentiation of Short, Single-Stranded DNA Homopolymers in Solid-State Nanopores, ACS Nano, 7, 4629 (2013) teaches that a difference in blockage current amount between bases is about 500 pA under a solution containing a 1M ion. The difference in blockage current amount positively depends on the electric conductivity of the nanopore, and when water is used as a solvent, as disclosed in Ralph M. M. Smeets, et al. Salt Dependence of Ion Transport and DNA Translocation through Solid-State Nanopores, Nano Lett. 6, 89, 2006, the electric conductivity is known to roughly linearly respond to the electrolyte concentration until about 1 mM. Hence, when the electrolyte concentration is reduced an order of magnitude, the difference in blockage current amount is also reduced an order of magnitude. The difference in blockage current amount between bases therefore gradually decreases to 50 pA at 100 mM, to 5 pA at 10 mM, and to 0.5 pA at 1 mM. On the other hand, high-frequency current noise generated during measurement can be largely classified into two types, i.e., noise derived from a device and noise derived from an amplifier. The noise derived from the device may be reduced by a measure such as capacitance reduction, but is less likely to be reduced to equal to or less than the noise derived from the amplifier. The lower limit of the electrolyte concentration is therefore defined by the noise derived from the amplifier. As disclosed in Adrian Balan, et al. Improving Signal-to-Noise Performance for DNA Translocation in Solid-State Nanopores at MHz Bandwidths, Nano Lett. 14, 7215, (2014), the noise derived from the amplifier is about 1 pA in an often-used frequency range (5 to 10 kHz). Hence, since 5 is often defined as a statistically significant signal-to-noise ratio, the lower limit of the electrolyte concentration needs to be 10 mM. On the other hand, there is no requirement that prevents the upper limit of the electrolyte concentration, and thus the electrolyte concentration is allowed to increase to the saturation concentration. That is, the ion concentration of the measurement solution is 10 mM or more and equal to or less than the saturation concentration.

In a desirable introduction procedure of the second solution, since the surface state of the thin film can be significantly changed by applying power to the thin film while the first solution is contained, the second solution is desirably introduced after a voltage of 0.1 V or more is applied to the thin film in the first solution. In a more preferable procedure, a high voltage is applied to the thin film being wetted by the first solution to open the nanopore by dielectric breakdown, and then the second solution is introduced. In this case, since a further high voltage is applied, the surface state of the film can be effectively changed to form the cation adsorption preventing structure, and thus RTN can be suppressed for a long time.

When the second solution is introduced, the concentration of the first solution is desirably sufficiently reduced. After introduction of the second solution, the concentration of the first solution is preferably 20% or less, more preferably 10% or less, and is specifically preferred to be 0.01 to 1%. In detail of the introduction procedure, for example, while the amount of the first solution is adjusted to be about 100 µL, the second solution is introduced by about 1000 µL, making it possible to sufficiently reduce the concentration of the first solution.

Figure 9:
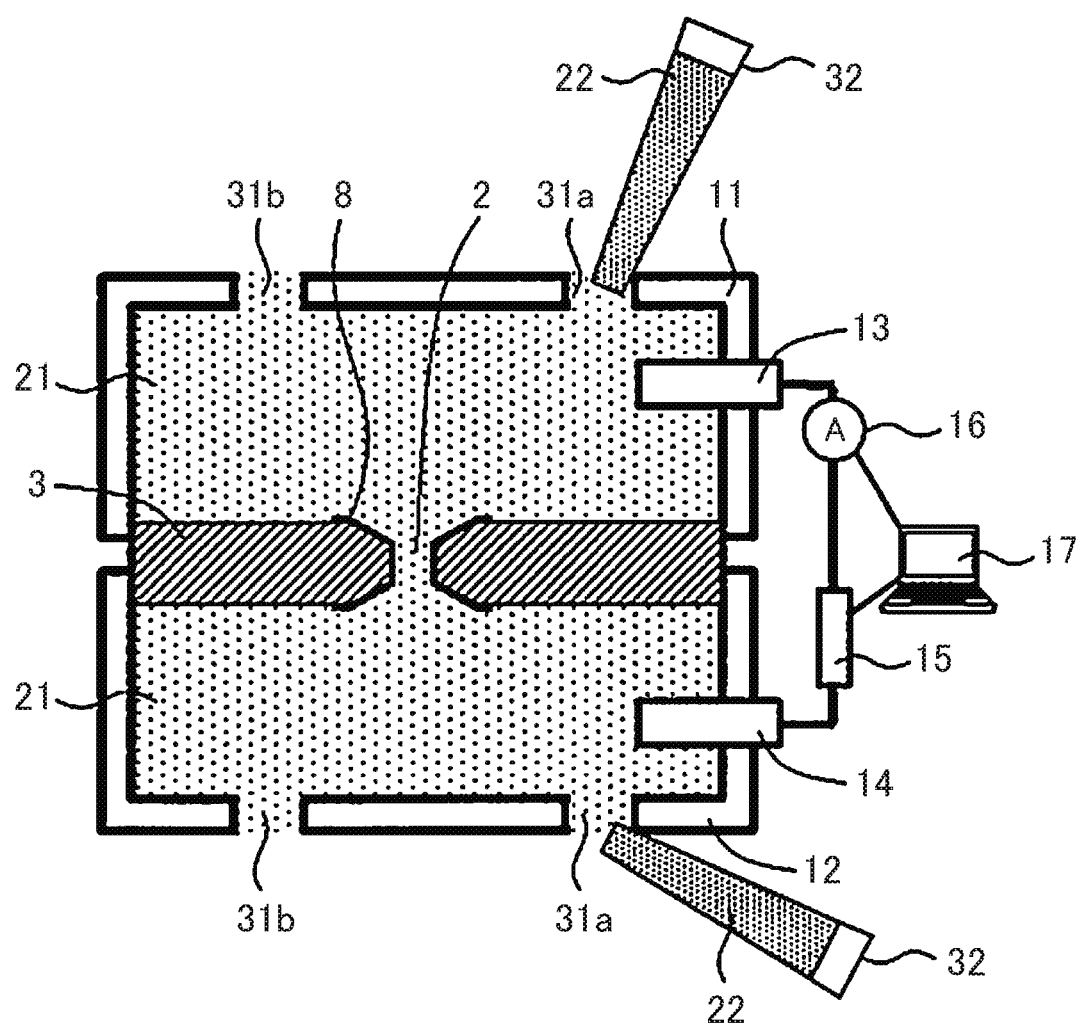
FIG. 9 is an explanatory drawing showing an exemplary method for replacing a first solution with a second solution.

FIG. 9 is an explanatory view showing an exemplary method for replacing the first solution with the second solution. For example, while the capacity of a solution tank is adjusted to be about 100 µL, an inlet 31*a* and an outlet 31*b* are provided in the solution tank as shown in FIG. 9. The first solution 21 is poured into the first tank 11 and the second tank 12, and the thin film 3 and the wall surface of the nanopore 2 are allowed to be wetted by the first solution 21 to form the cation adsorption preventing structure 8, and then the second solution 22 is introduced from the inlet 31*a* by a pipet 32 or the like. Since the first solution 21 can be overflown from the outlet 31*b* through such operation, the concentration of the first solution 21 can be more efficiently reduced by collecting the overflown solution. Alternatively, the first solution 21, which has been contained by 100 µL in the solution tank, is collected and decreased to about 10 µL, and then the second solution 22 is introduced by about 1000 µL, making it possible to more efficiently reduce the concentration of the first solution 21. The second solution 22 may be poured after the first solution 21 is entirely collected. This can more securely prevent the first solution 21 from remaining. On the other hand, bubbles tend to form in the vicinity of the nanopore 2 during introduction of the solution. Hence, the second solution 22 is poured while the first solution 21 in the vicinity of the nanopore 2 remains, which more effectively suppresses babble formation during introduction of the second solution 22. A monitor capable of measuring the concentration may be provided in the solution tank in order to determine whether the first solution 21 is sufficiently replaced with the second solution 22.

In a possible arrangement, the first solution being a solution containing an ion of a group II element or an acidic solution may fill only one of the first and second tanks 11 and 12 so as to eliminate the need of preparing a large amount of that solution, and the other tank is filled with a third solution different in electrolyte type or concentration from the first solution 21. Even if only the tank on one side is filled with the first solution, since the cation adsorption preventing structure 8 can be provided by wetting the wall surface of the nanopore, the RTN reduction effect is given. Such an arrangement eliminates the need of preparation of a large amount of first solution particularly in a structure of arrayed nanopores, and advantageously allows cost reduction when cost of the first solution is higher than that of the third solution. More preferably, the third solution contains an ion of a group I element, and the first solution and the third solution are allowed to wet the thin film and the wall surface of the nanopore, and then the second solution is introduced into the first solution.

Figure 10:
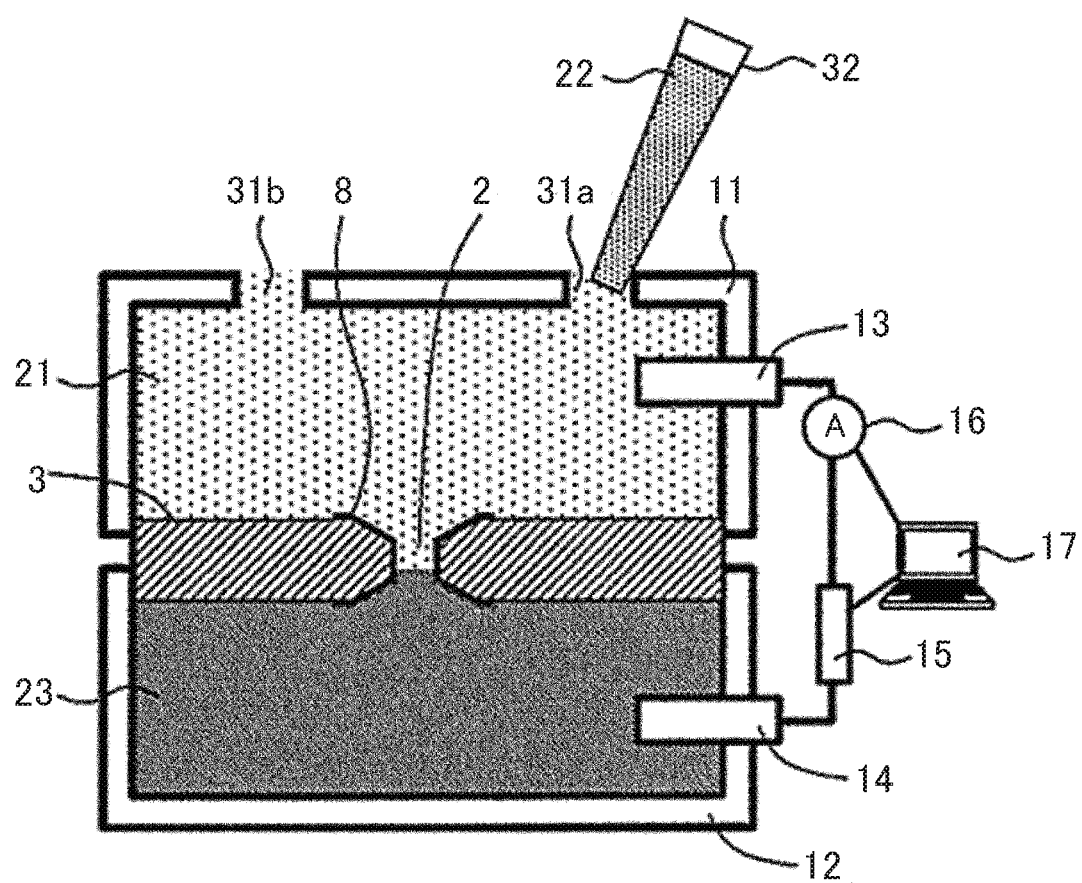
FIG. 10 is a schematic sectional view showing an exemplary configuration of the current measuring apparatus.

FIG. 10 is a schematic sectional view showing an exemplary configuration of a current measuring apparatus suitable for performing the above-described procedure. The first tank is filled with the first solution 21 being a solution containing an ion of a group II element or an acidic solution, and the second tank 12 is filled with a third solution 23 containing an ion of a group I element. In this case, the second solution 22 containing an ion of a group I element such as Cs may be introduced only into the first tank 11 after the cation adsorption preventing structure 8 is formed. Since the third solution 23 filling the second tank 12 already contains a group I element, the second solution 22 needs not be further introduced into the second tank 12. Such a configuration allows the solution introduction mechanism to be provided only in the first tank 11 to be filled with the first solution, leading to a simple apparatus configuration.

In a more preferable procedure, while the first tank 11 is filled with the first solution 21 being a solution containing an ion of a group II element or an acidic solution, and while the second tank 12 is filled with the third solution 23 containing an ion of a group I element, a high voltage is applied to the thin film 3 to open the nanopore 2 by dielectric breakdown, and then the second solution 22 is introduced only into the first tank 11. In this case, since a further high voltage is applied to the thin film 3, the surface state of the film is efficiently changed to form the cation adsorption preventing structure 8, making it possible to suppress RTN for a long time. When the surface state is thus changed by applying power to the film by voltage application, a direction of the voltage applied during changing of the surface state is preferably adjusted to correspond to a direction of the voltage during measurement of the ion current flowing through the nanopore 2.

In an exemplary specific measurement procedure, when the nanopore 2 is opened by dielectric breakdown, the first tank 11 is filled with the first solution 21, the second tank 12 is filled with the third solution 23, and the first electrode 13 provided in the first tank 11 has a reference potential, 0 V, a positive voltage $+V_1$ [V] is applied to the second electrode 14 provided in the second tank 12 to apply power to the film surface. When the ion current flowing through the nanopore 2 is then measured, it is desirable that the second solution 22 is introduced into the first tank 11, and a positive voltage $+V_2$ [V] is applied to the second electrode 14 to measure the ion current. The biopolymer 51 is desirably contained in the first tank 11 to obtain the blockage current of the biopolymer.

Figure 11:
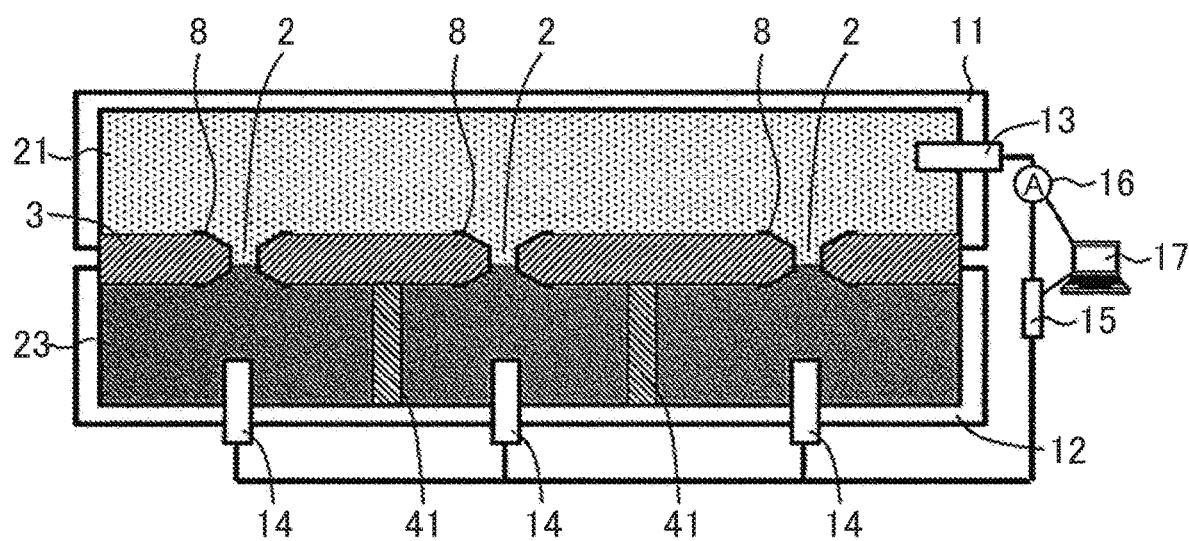
FIG. 11 is a schematic sectional view showing an exemplary configuration of a current measuring apparatus having a nanopore array.

More preferably, the above configuration using the third solution 23 is applied to a structure having arrayed nanopores 2. FIG. 11 is a schematic sectional view showing an exemplary configuration of a current measuring apparatus having a nanopore array. The first tank 11 and the second tank 12 are separated by the thin film 3 having a plurality of nanopores 2. The first tank 11 configures one common tank for the plurality of nanopores 2. On the other hand, the second tank 12 is divided into a plurality of individual tanks corresponding to the individual nanopores. One first electrode (common electrode) 13 is disposed in the common tank, and one individual electrode is disposed in each of the individual tanks.

In a probable configuration for the nanopore array, as shown in FIG. 11, there are a first solution filling the individual tanks independently provided for the respective nanopores 2 of the thin film 3, and a second solution filling the common tank for the nanopores 2. The first and second solutions individually filling each nanopore 2 are desirably disposed so as to have different potentials from each other, and the individual tanks are partitioned from one another by insulative partition walls 41. The material of the insulative partition walls 41 may be any one of a solid, a liquid, and a gas. For example, in the case of the solid, the tanks are partitioned by a resin such as PMMA, preferably polyimide, Teflon (registered trademark), or the like having a high chemical resistance. When the partition walls 41 are made of a liquid, and when a solvent of the solution individually filling the nanopore 2 is water, for example, an organic solvent is preferably used so as not to be compatible with water. The partition walls 41 may be made of a gas such as air or $N_2$ for isolation.

Such a configuration having the common solution advantageously simplifies a solution introduction mechanism compared with a configuration in which individual solutions fill above and below all the nanopores 2. In addition, the configuration advantageously allows the blockage currents of biopolymers to be simultaneously obtained in all the nanopores simply by allowing only the common solution to contain the biopolymer. As shown in the configuration of FIG. 11, the third solution 23 is used as the individual solution filling the individual tanks partitioned by the partition walls 41, and the first solution 21 is used as the common solution filling the common tank. Consequently, the second solution 22 may be introduced only into the first solution 21, and the biopolymer is desirably contained in the second solution 22 when the blockage current of the biopolymer is obtained.

The group I element contained in the third solution is desirably Cs in order to increase the signal amount during analysis of the biopolymer. For the Cs ion concentration, a lower limit of the electrolyte concentration is preferably set in light of a signal-to-noise ratio. In this example, the lower limit of the electrolyte concentration needs to be 10 mM. On the other hand, there is no factor that prevents the upper limit of the electrolyte concentration, and thus the electrolyte concentration is allowed to increase to the saturation concentration. That is, the Cs ion concentration of the measurement solution is 10 mM or more and equal to or less than the saturation concentration. Preferably, the Cs ion concentration is 0.1 mM or more and equal to or less than the saturation concentration. The nanopore array structure as shown in FIG. 11 advantageously makes it possible to drastically increase the throughput of the measurement. In the nanopore array structure, the nanopores 2 are preferred to be regularly arranged. The arrangement interval of the nanopores can be adjusted to 0.1 to 10 µm, preferably 0.5 to 4 µm, depending on an electrode to be used, capacity of an electric measurement system, or a processing limit of a semiconductor process.

There is now described in detail an exemplary configuration of an apparatus to achieve the current measurement including the procedure for introducing the second solution into the first solution as described above.

Figure 12:
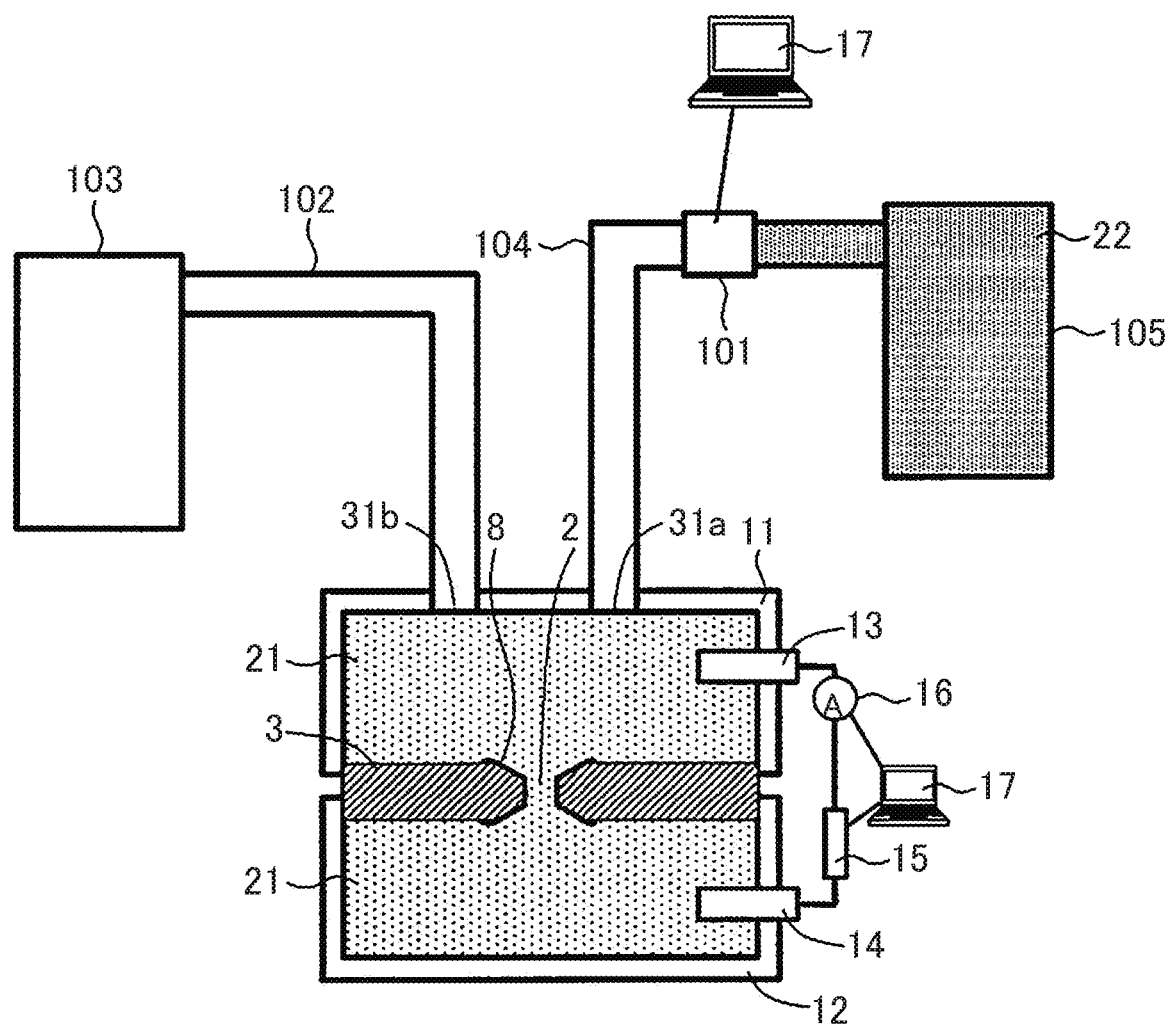
FIG. 12 is a diagrammatic illustration showing an exemplary configuration of a current measuring apparatus.

FIG. 12 is a diagrammatic illustration showing an exemplary configuration of a measuring apparatus having a mechanism to introduce the second solution 22 into the first solution 21. A solution tank, into which at least the first solution 21 is introduced, has an inlet 31a to introduce the second solution 22, and preferably has an outlet 31b such that the first solution 21 can be discharged to the outside by introducing the second solution 22. A discharge channel 102 may be provided while continuing from the outlet 31b, and may communicate with a waste tank 103. The inlet 31a to introduce the second solution 22 may communicate with an injection channel 104, and the injection channel 104 desirably communicates with a third tank 105 storing the second solution 22.

A fluid controller 101 is desirably provided to transport the second solution 22. The fluid controller 101 may be specifically configured to pump out a fluid, or may be configured of valves. The fluid controller 101 may be provided in any one of the injection channel 104, the discharge channel 102, the third tank 105, and the waste tank 103. In an exemplary possible mechanism, the fluid controller 101 is provided in the discharge channel 102 or the waste tank 103 to develop a negative pressure in the waste tank 103 or the discharge channel 102 so that the second solution 22 is transported. The fluid controller 101 pours the solution at a flow rate of 10 mL/s or less, for example. The solution is poured at a relatively slow inflow rate, preferably 100 µL/s or less, more preferably 10 µL/s or less. This makes it possible to prevent breakage of the thin film 3 due to turbulence or water pressure in the vicinity of the thin film 3. The fluid controller 101 may be controllably connected to a personal computer 17 or the like so as to allow the second solution 22 to be introduced into the solution tank containing the first solution 21 at a given timing.

In the exemplary configuration of FIG. 12, since any of the solutions filling both sides of the thin film 3 is the first solution 21, the introduction mechanism of the second solution 22 desirably introduces the second solution into both sides of the thin film 3. In a more preferable configuration, the first solution 21 fills only one side of the thin film 3, for example, only the first tank 11, and the second tank 12 is filled with the third solution 23. This configuration advantageously eliminates the need of the mechanism to introduce the second solution 22 into the third solution 23, leading to a simple apparatus mechanism. The individually poured third solution 23 preferably contains a group I element, and more preferably contains Cs as the group I element.

Figure 13:
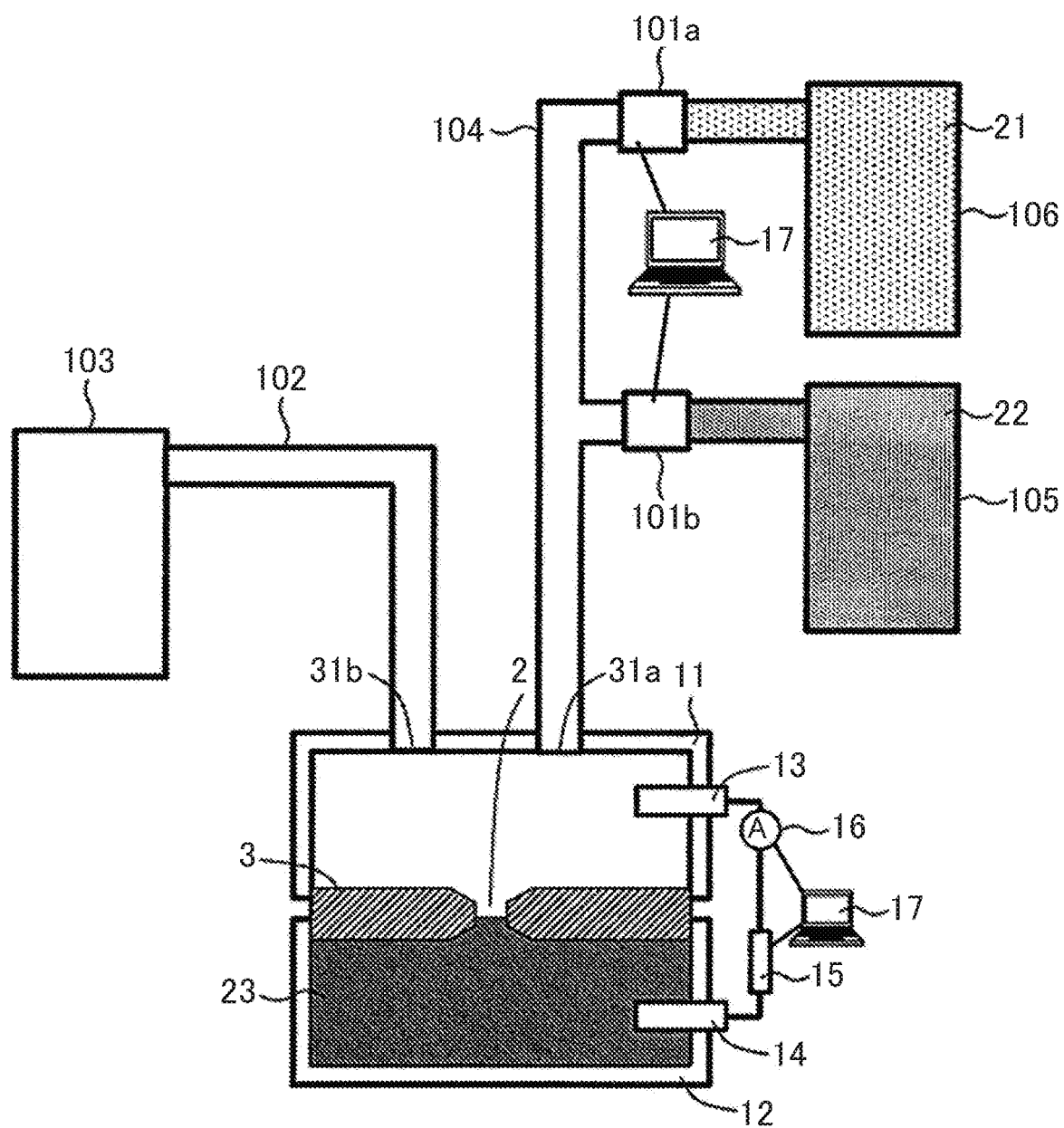
FIG. 13 is a diagrammatic illustration showing another exemplary configuration of a current measuring apparatus.

FIG. 13 is a diagrammatic illustration showing another exemplary configuration of the measuring apparatus having a mechanism to introduce the second solution 22 into the first solution 21. It is more desirable that a fourth tank 106 storing the first solution 21 is prepared as in this exemplary configuration, and a mechanism to introduce the first solution 21 is provided as with the second solution 22.

The reason why this configuration is preferable is described below. For example, when the measuring system of this example is used at a given user while the configuration of FIG. 12 is used, the system may be delivered from a distributer to the user while solutions, which are beforehand introduced into two sides of the thin film 3, fill the solution tanks on the two sides. However, if the system is shipped or left for a long time while the solution fills the solution tank on either side of the thin film 3, a hole is disadvantageously formed in the thin film 3 due to a potential difference between the solutions filling the two sides of the thin film 3 (Matsui, K., Yanagi, I., Goto, Y. & Takeda, K. Prevention of dielectric breakdown of nanopore membranes by charge neutralization. Sci. Rep. 5, 17819 (2015)), or a hole is disadvantageously formed due to oxidation or etching of the thin film 3 by the solutions. Hence, the system is more preferably shipped in a state where the solution is introduced only into one side of the thin film 3 as in the exemplary configuration of FIG. 13, or in a dried state where no solution has been introduced into each tank. In such a case, the solution is introduced into the other side or each side of the thin film 3 by the user. Hence, the fourth tank 106 is prepared so as to store the first solution 21 as in FIG. 13, making it possible to achieve a mechanism to fill each side of the thin film 3 with the solution by the user. Fluid controllers 101*a* and 101*b* are provided between the third tank 105 and the injection channel 104 and between the fourth tank 106 and the injection channel 104, respectively.

Figure 14:
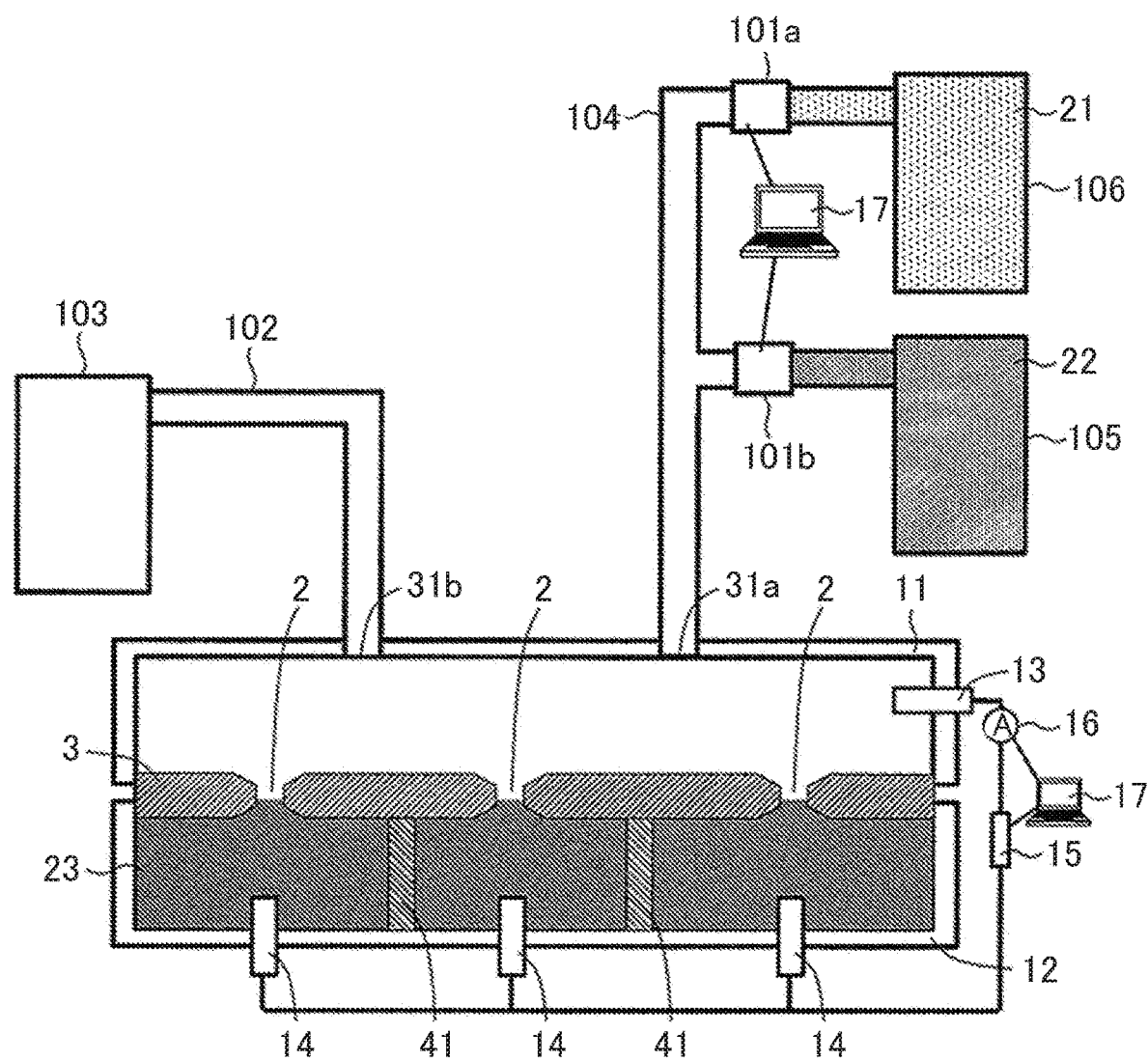
FIG. 14 is a schematic view showing another exemplary configuration of a current measuring apparatus.

FIG. 14 is a schematic view showing another exemplary configuration of the measuring apparatus of this example. The thin film 3 having the nanopore 2 desirably has arrayed nanopores 2 as in FIG. 14 so that throughput can be improved. The solution individually filling a plurality of individual tanks provided in the second tank 12 may be the first solution 21 but is preferably the third solution 23. This configuration eliminates the need of the mechanism to introduce the second solution 22 into the third solution 23, leading to a simple apparatus mechanism. The third solution 23 filling the individual tanks preferably contains a group I element, and more preferably contains Cs as the group I element.

Herein described is an exemplary procedure for introducing the solution into the measuring apparatus of FIG. 14. In the state of FIG. 14, the fluid controller 101*a* is used to introduce the first solution 21 from the fourth tank 106 to the first tank 11 through the injection channel 104. At this time, the first solution 21 may be introduced up to the discharge channel 102 or the waste tank 103. This operation causes each nanopore 2 of the thin film 3 to be wetted by the first solution 21, leading to formation of the ion adsorption preventing structure on the wall surface of the nanopore 2. A voltage is preferably applied between the first electrode (common electrode) 13 disposed in the first tank 11 and the plurality of second electrodes (individual electrodes) 14, which are disposed in the plurality of individual tanks formed by partitioning the second tank 12, to efficiently form the ion adsorption preventing structures. Subsequently, the fluid controller 101*b* is used to introduce the second solution 22 from the third tank 105 to the first tank 11 through the injection channel 104. At this time, the first solution 21 that has filled the first tank 11 is introduced into the waste tank 103 through the discharge channel 102, and thus most of the inside of the first tank 11 is refilled with the second solution 22 as a replacement. The second solution 22 may be introduced up to the discharge channel 102 or the waste tank 103.

A solution introduction procedure for the measuring apparatus having the third tank 105, the fourth tank 106, and the array device has been described hereinbefore. The solution may be introduced in a procedure similar to this procedure for the measuring apparatus of FIG. 12 or 13, for example. The solution introduction procedure described using FIG. 14 is simply an exemplary procedure and is not limitative. For example, the introduction amount of the first or second solution 21 or 22 is not limited to the above-described amount. Although each nanopore 2 is opened before introduction of the first solution 21 in the exemplary configuration of FIG. 14, it is more preferable that the first solution is introduced to the thin film 3 having no nanopore 2, and then the nanopore 2 is opened by dielectric breakdown.

The material of the solution tank such as the first tank 11, the second tank 12, the third tank 105, the fourth tank 106, or the waste tank 103 may be, for example, PMMA, or may include Teflon having a high chemical resistance. A solution tank having a capacity of, for example, 100 mL or less is used as each solution tank. The material of the channel such as the injection channel 104 or the discharge channel 102 may be, for example, PMMA, or Teflon having a high chemical resistance. For example, a channel having a total length of 1 m or less and a diameter of 1 cm or less is used as the injection channel 104 or the discharge channel 102.

The solution such as the first solution 21, the second solution 22, or the third solution 23 may be provided together with an instruction manual describing a using procedure or usage amount of the solution. A usable solvent of the solution includes a solvent that can stably disperse the biopolymer, does not dissolve each electrode, and does not disturb electron transfer with the electrode. For example, the solvent includes water, alcohols (such as methanol, ethanol, and isopropanol), acetic acid, acetone, acetonitrile, dimethylformamide, and dimethyl sulfoxide. When nucleic acid is measured as a biopolymer, water is most preferable as the solvent. Each solution may be provided while being fully contained in the solution tank, or may be provided while being enclosed in a pack or a liquid tank so as to be supplemented or poured as a replacement into each of the first to fourth tanks as necessary. The solution may be provided in an immediately usable state (liquid), provided as a condensed liquid to be diluted by an appropriate solvent in use, or provided in a solid state (for example, powder) to be reconstituted by an appropriate solvent in use. Such form and preparation of the solution can be understood by those skilled in the art.

The system to measure the current and the system to introduce the solution are not necessarily provided in the same apparatus. For example, the current measuring apparatus and the solution introduction apparatus may be separated and provided as individual apparatuses.

Exemplary experiments to verify the effects of this example are described below.

When RTN is assumed to be derived from the ion desorption/adsorption phenomenon on the wall surface having the nanopore and in the vicinity of the wall surface as described before, RTN is considered to be derived from a phenomenon caused by desorption/adsorption of a cation on a silanol group surface for a SiN thin film typically used for a nanopore, for example. In general, the selectivity coefficient of the silanol group is known to be as follows: Li<Na<K<Rb<Cs<group II element (Ca, Ba). A cation species such as Li, which is less likely to adsorb to the silanol group, is probably stabilized in a desorption state from the silanol group surface. On the other hand, a cation species such as Ca or Ba, which is likely to adsorb to the silanol group, is probably stabilized in an adsorption state to the silanol group surface.

Figure 15:
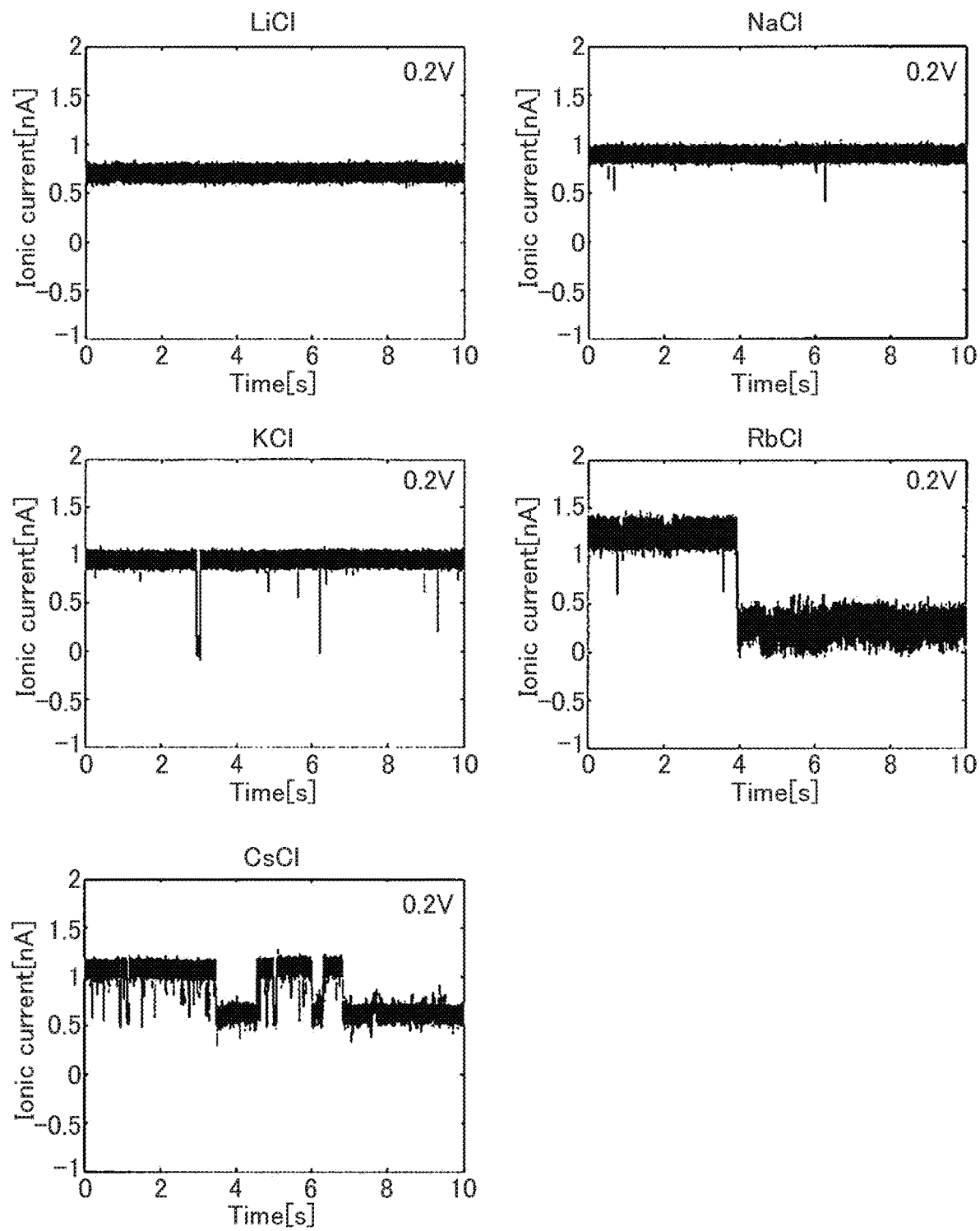
FIG. 15 includes views each showing an exemplary base current in a solution containing a group I element.

FIG. 15 include views each showing an exemplary base current in a solution containing a group I element. The first tank 11 and the second tank 12 of the measuring apparatus of FIG. 8 were each filled with a neutral solution containing LiCl, NaCl, KCl, RbCl, or CsCl having a concentration of 1 M, and a nanopore 2 about 1 to 10 nm in size was opened by dielectric breakdown in a SiN thin film having a thickness of about 5 to 10 nm. Subsequently, a voltage of 0.2 V was applied between the first electrode 13 and the second electrode 14 to measure an ion current flowing through the nanopore. From the results of FIG. 15, it has been found that RTN is amplified in a relation of Li<Na<K<Rb<Cs, which supports the above-described hypothesis.

Figure 16:
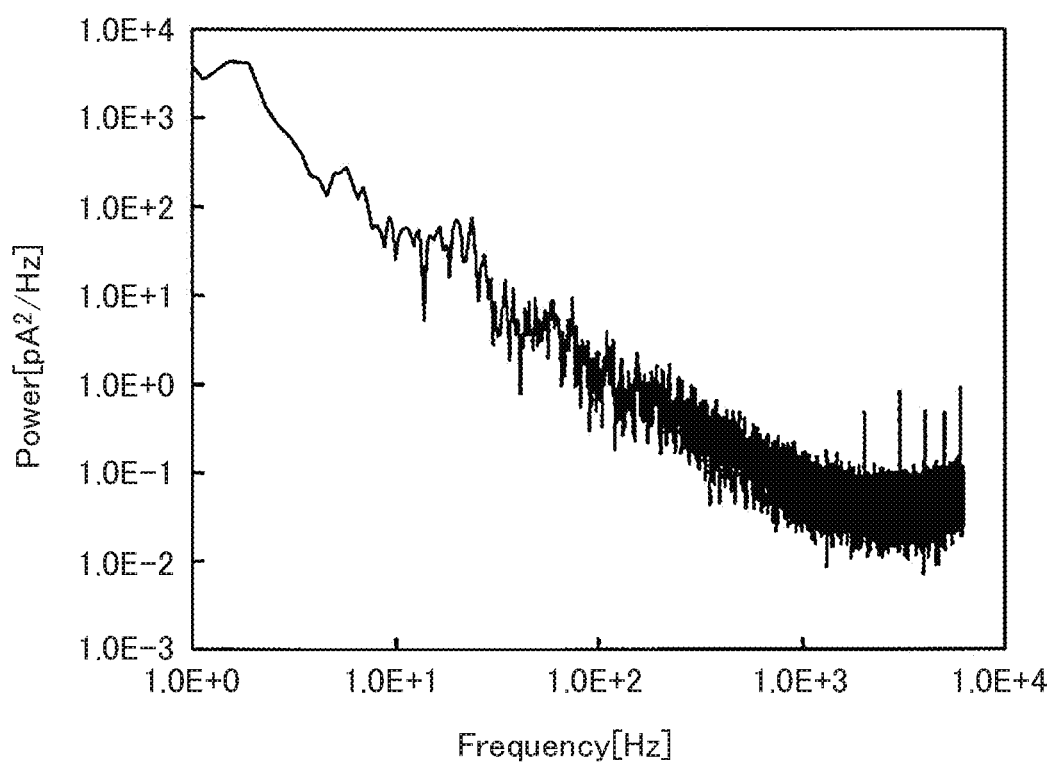
FIG. 16 shows experimental results of power spectrum density obtained from base current waveforms.

RTN may be evaluated not only using the waveform of the base current but also using power spectral density. In most reports on nanopore sequencers, RTN typically transitions between a plurality of levels, and thus corresponds to a composite RTN including a large number of pieces of RTN that transitions between two levels. The power spectral density of the RTN that transitions between two levels is known to be of a Lorentz type in which the density decays directly with $1/f^2$ in logarithmic expression, and is called $1/f^2$ noise. For the composite RTN, since $1/f^2$ noises having various time constants are observed in a superimposed manner, the power spectral density corresponds to superposition of a plurality of Lorentz curves, and decays directly with $1/f^\alpha$ ($0<\alpha<2$, $\alpha\approx 1$) in logarithmic expression, and is represented by the following expression (Heerema S. J., et al., 1/f noise in graphene nanopores, Nanotech. 26(7), 074001 (2015)).

$$S(f)=C_{lf}I^2/f^\alpha \qquad \text{Expression 1}$$

f: frequency
S(f): power spectral density
$C_{lf}$: low-frequency noise coefficient
I: current value
α: coefficient The noise amount can be evaluated through relative comparison of $C_{lf}$, i.e., larger $C_{lf}$ means larger noise. Consequently, a power spectral density as in FIG. 16 is obtained from the base current waveforms shown in FIG. 15, and $C_{lf}=S(1\text{ Hz})/I^2$ is calculated from the power spectral density, thereby the noise amount can be quantitatively evaluated.

Figure 17:
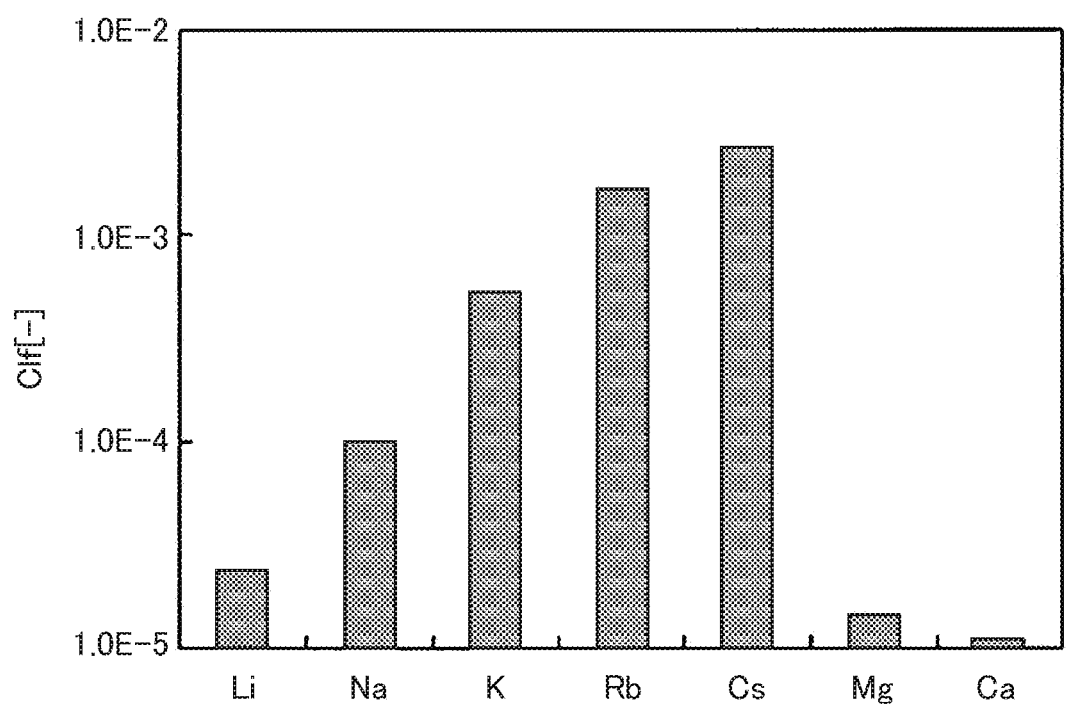
FIG. 17 shows experimental results of $C_{if}$ values measured with various elements.

FIG. 17 shows experimental results of the $C_{lf}$ values measured with various elements. In FIG. 17, a nanopore was opened in a SiN thin film by dielectric breakdown using each of neutralized 1M LiCl, 1M NaCl, 1M KCl, 1M RbCl, 1M CsCl, 1M MgCl$_2$, and 1M CaCl$_2$, and $C_{lf}$ values were obtained three times being the number of times N of experiments, and the averages of the values were compared to one another. As a result, $C_{lf}$ was found to vary with the group I elements: Li<Na<K<Rb<Cs, and found to be low for the group II element such as Ca or Ba compared with Cs. These results support our hypothesis on RTN.

A neutralized solution containing a group I element is typically used as the DNA measurement solution. In particular, the solution containing K, Rb, or Cs as the group I element is known to have a high electric conductivity. Of these, Cs has a high solubility in water, and electric conductivity of the solution can be increased by increasing the concentration of Cs. However, as shown in FIGS. 15 and 17, RTN contained in the measurement solution was found to vary in a relation of Li<Na<K<Rb<Cs. That is, while amplification of the signal level by Cs antinomically amplifies RTN in the existing method, amplification of the signal level and a reduction in RTN were confirmed to be achieved together only by the RTN reduction method of this example.

Figure 18:
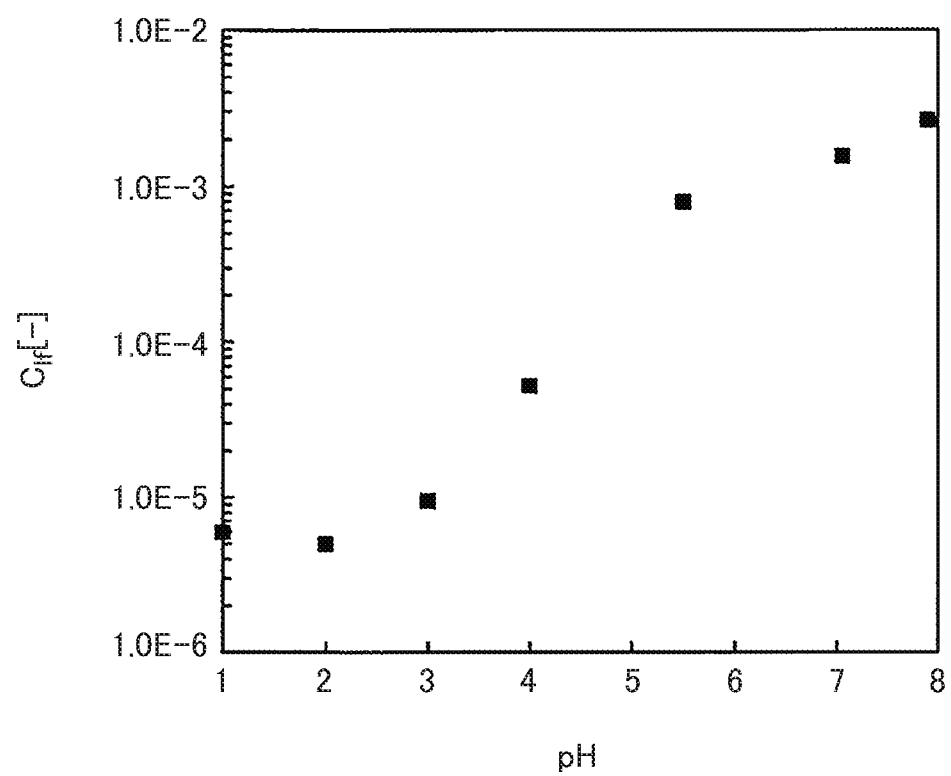
FIG. 18 shows experimental results of $C_{if}$ values measured with different pH values.

If the hypothesis of the RTN generation mechanism is true, it is considered that H is saturated and stabilized while adsorbing to a silanol group at a low pH condition. A nanopore was therefore opened in a SiN thin film by dielectric breakdown while pH of 1M CsCl was varied within a range from 1 to 8, and $C_{lf}$ values were obtained three times being the number of times N of experiments, and the averages of the values were compared from one another. FIG. 18 shows experimental results of the $C_{lf}$ values measured with different pH values. As shown in FIG. 18, $C_{lf}$ was found to extremely decrease in pH of 5.5 or less compared with a neutral condition of pH of about 7 to 8. These results also support the hypothesis.

Figure 19:
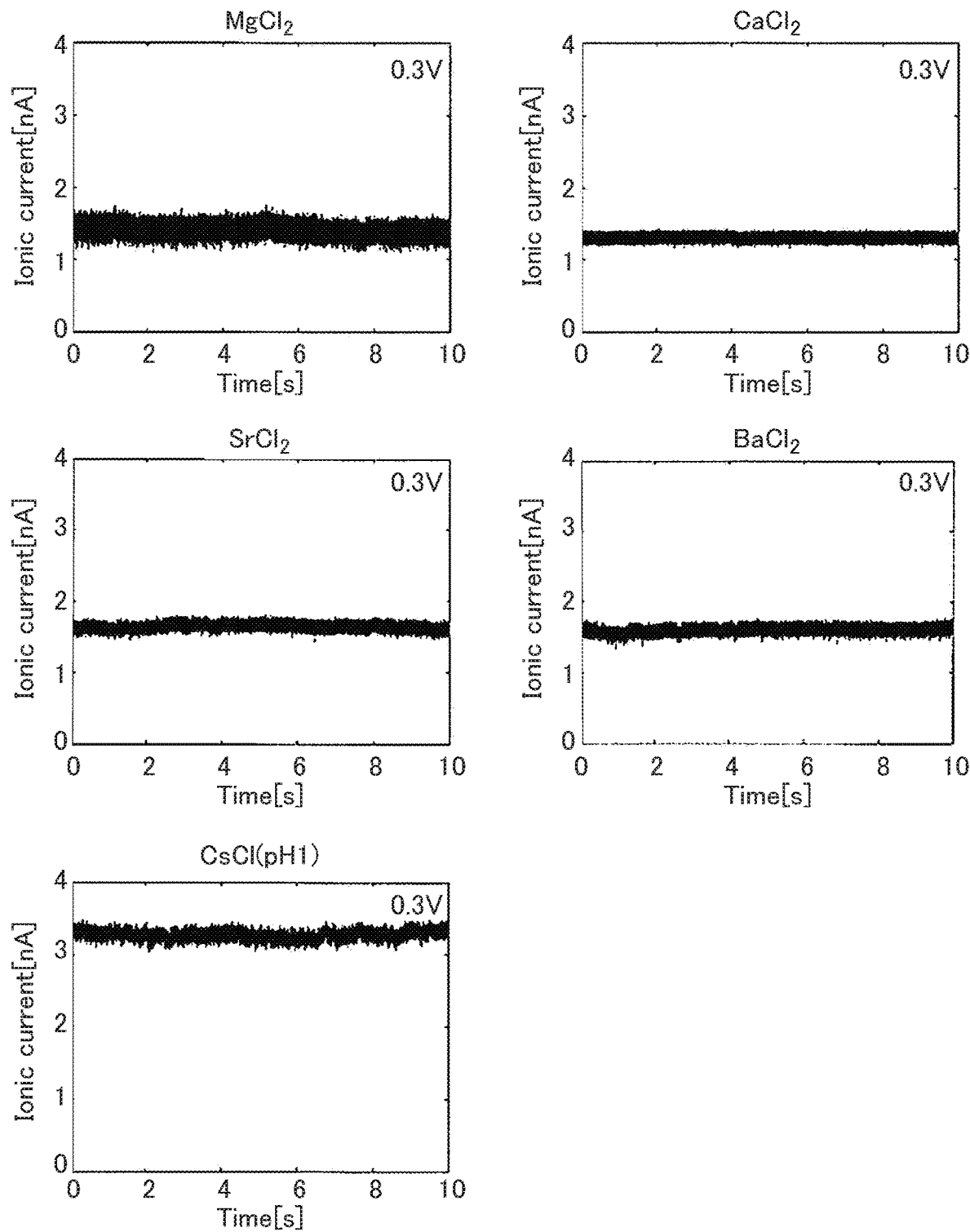
FIG. 19 includes views each showing an exemplary base current when a nanopore is opened using the first solution.

To summarize the condition for reducing RTN, FIGS. 17 and 18 reveal that RTN decreases for a group II element or an acidic solution. FIG. 19 includes views each showing an exemplary base current when a nanopore is opened using 1M MgCl$_2$, 1M CaCl$_2$, 1M SrCl$_2$, or 1M BaCl$_2$ including the above-described group II element, or using 1M CsCl (pH 1) being an acidic solution. The applied voltage is 0.3 V during measurement of the base current. As shown FIG. 19, the RTN reduction effect was also confirmed from the current waveforms. To compare between the group II elements, since Mg is small in selectivity coefficient of the silanol group among the four elements of Mg, Ca, Sr, and Ba and thus tends to induce RTN, Ca, Sr, or Ba can relatively reduce RTN. Since $C_{lf}$ tends to decrease as pH is smaller as shown in FIG. 18, a relatively small pH is preferably selected in a range of pH of 5.5 or less to further reduce RTN by the acidic solution.

Figure 20:
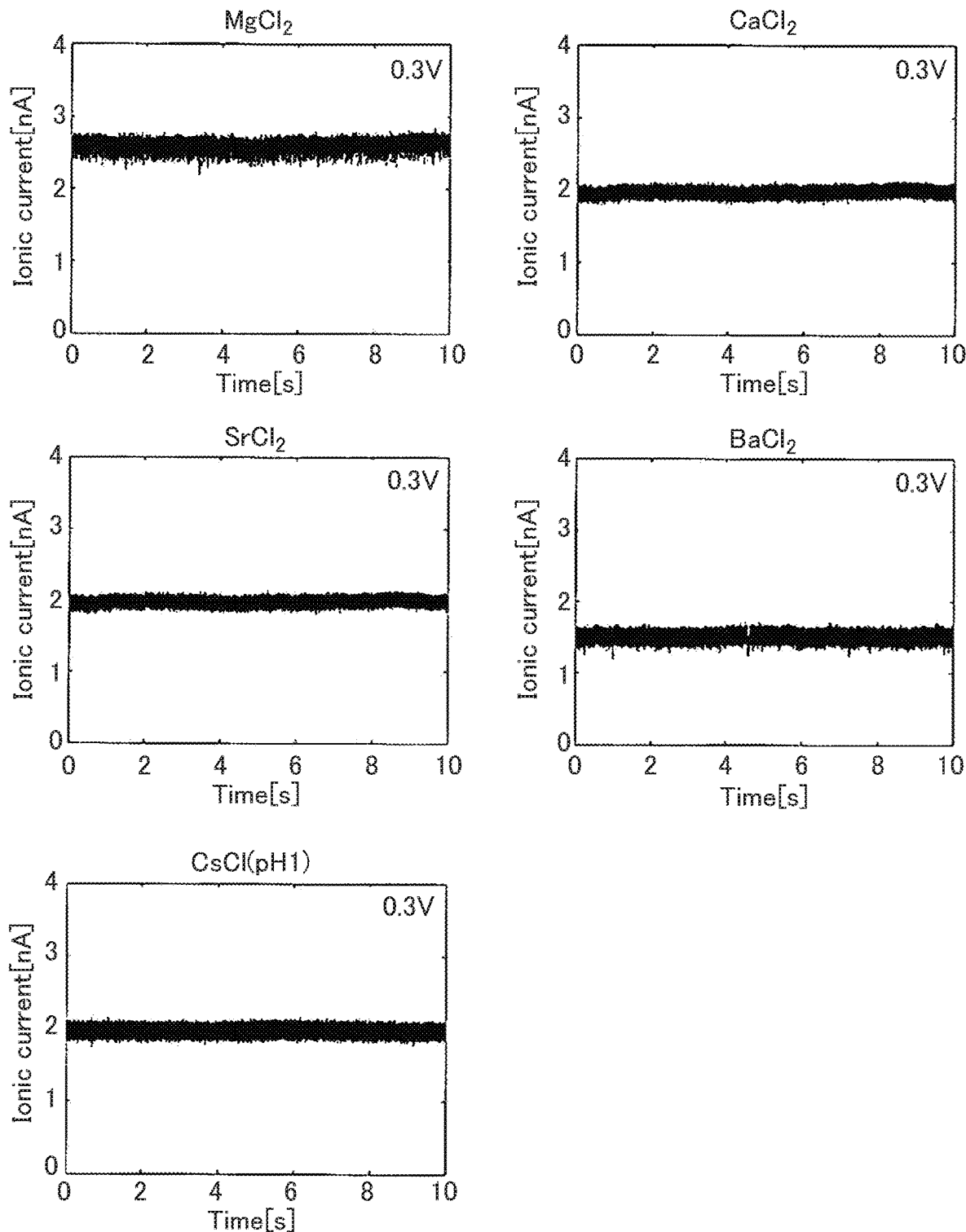
FIG. 20 includes views each showing experimental results of a base current when an RTN reduction procedure is performed.

FIG. 20 includes views each showing a base current when a 1M CsCl (pH 8) solution is introduced after a nanopore is formed by dielectric breakdown by applying a high voltage to the SiN film via the solution containing an ion of a group II element or the acidic solution as shown in FIG. 19. The applied voltage is 0.3 V during measurement of the base current. As shown in FIG. 20, RTN is suppressed even after introduction of Cs that tends to generate RTN. Hence, it has been found that the nanopore wall surface can be covered with the group II element or H to prevent desorption/adsorption of another cation species such as Cs. The generation mechanism of RTN was verified and the suppression method of RTN was found through the above experiments.

Figure 21:
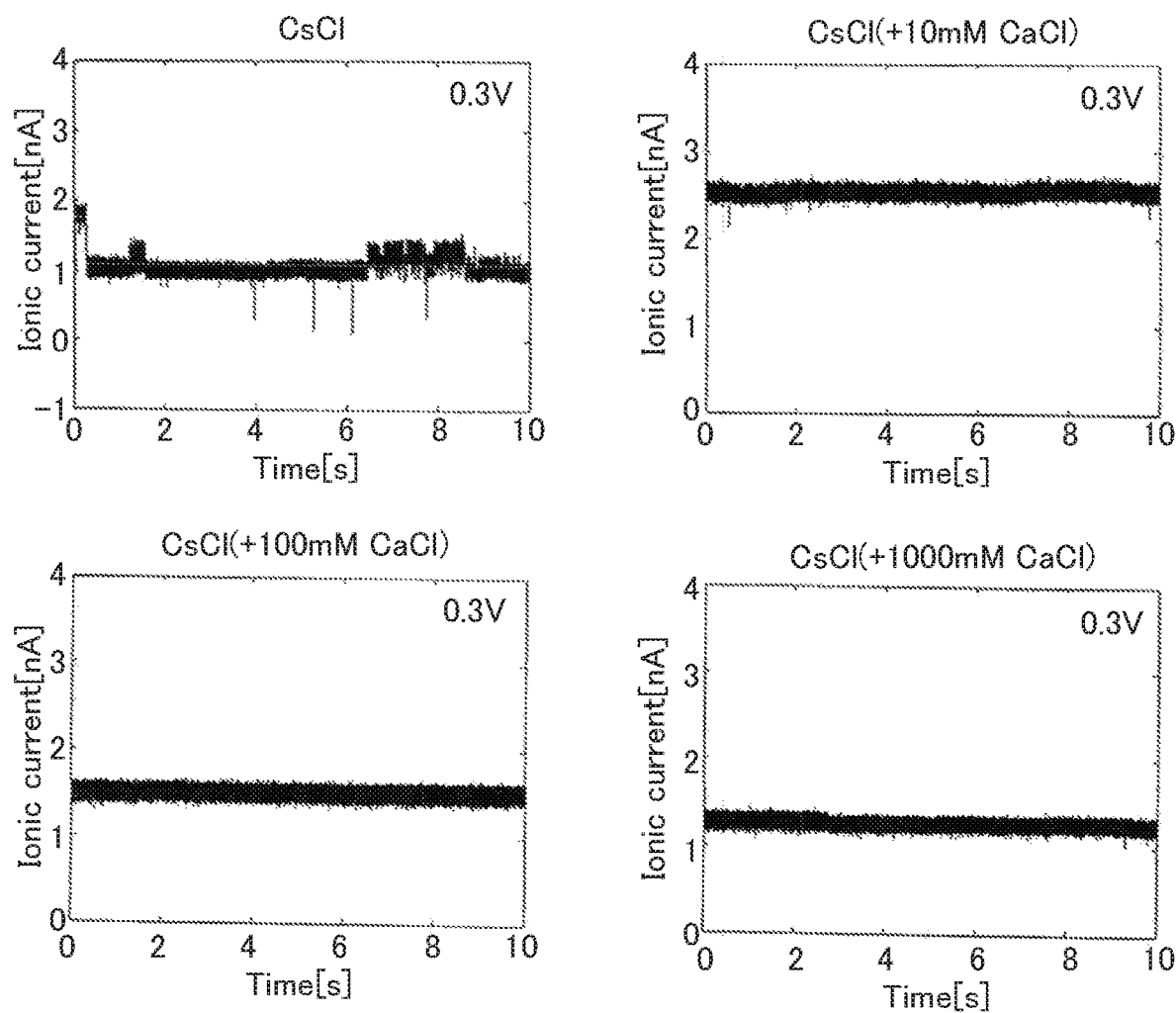
FIG. 21 includes views showing verification results on a lower limit of concentration of a group II element in the first solution.

FIG. 21 includes views showing verification results on the lower limit of concentration of the group II element when RTN is reduced by the group II element. FIG. 21 shows a base current when a nanopore is opened by dielectric breakdown at four conditions of 1M CsCl containing no CaCl$_2$, 1M CsCl containing 10 mM CaCl$_2$, 1M CsCl containing 100 mM CaCl$_2$, and 1M CsCl containing 1M CaCl$_2$., and then a 1M CsCl solution containing no CaCl$_2$ is introduced. The applied voltage is 0.3 V during measurement of the base current. As known from these results, when the group II element of 10 mM or more is contained in the solution, the RTN suppression effect is exhibited, and thus the concentration of the group II element is desirably adjusted to 10 mM or more and equal to or less than the saturation concentration.

Figure 22:
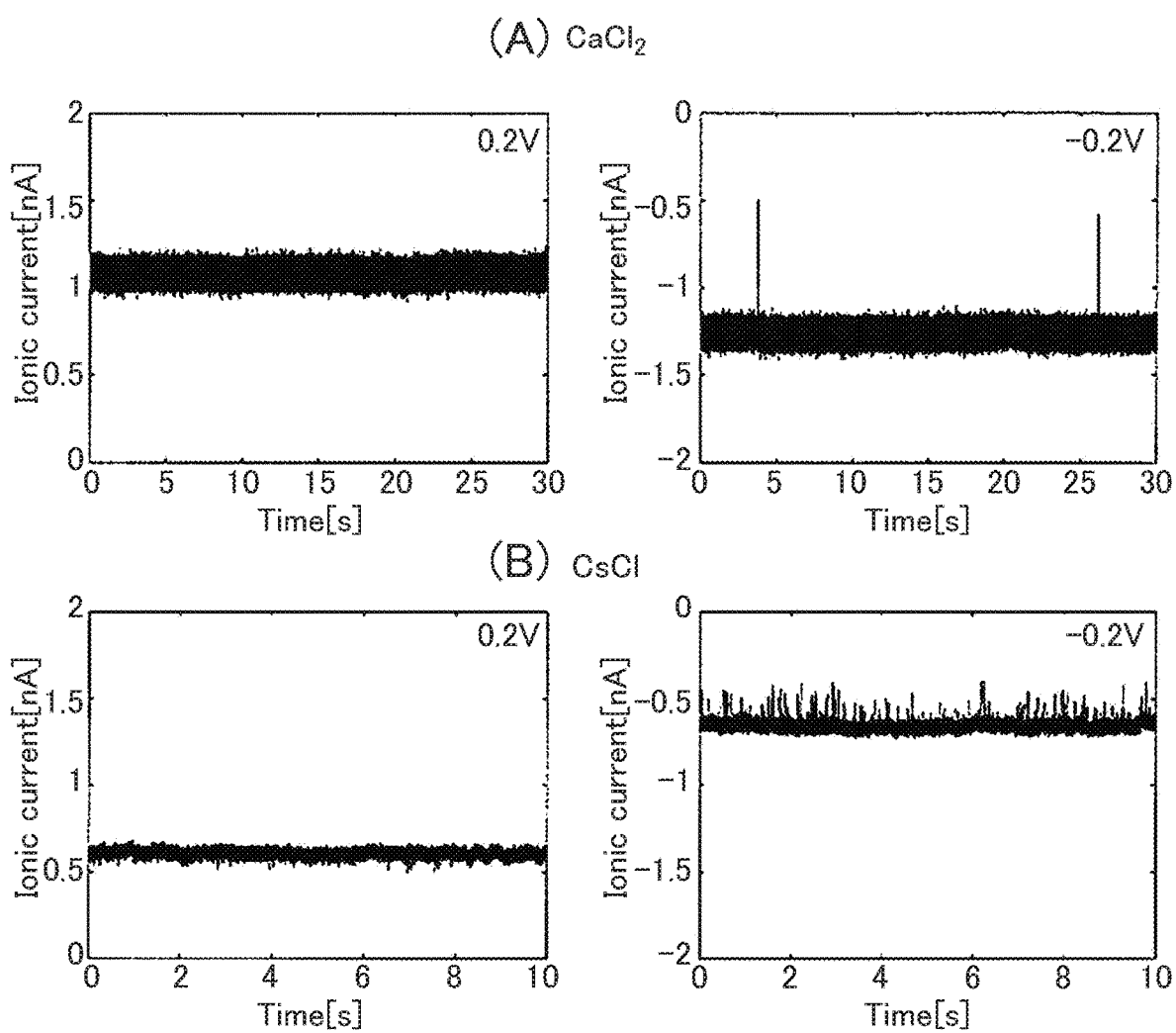
FIG. 22 includes views showing experimental results when abase current is measured while a direction of an applied voltage is varied.

FIG. 22 includes views showing verification results of a direction of the applied voltage. FIG. 22(A) shows abase current when a positive high voltage (+5 to 10 V) is applied to the SiN film via a CaCl$_2$ solution to form a nanopore by dielectric breakdown, and then a positive voltage (+0.2 V) and a negative voltage (−0.2 V) are applied. The direction of the applied voltage is equal to that in nanopore formation for the positive voltage and is opposite to that in nanopore formation for the negative voltage. As shown in FIG. 22(A), it has been found that RTN generation can be more suppressed at positive voltage application than at negative voltage application. FIG. 22(B) shows a base current when a positive high voltage (+5 to 10 V) is applied to the SiN film via the CaCl$_2$ solution to form a nanopore by dielectric breakdown, and then a CsCl solution is introduced and a positive voltage (+0.2 V) and a negative voltage (−0.2 V) are applied. In this case, it is also known that RTN generation can be suppressed by adjusting the direction of the applied voltage in the ion current measurement to be equal to that in the nanopore formation. As known from such a result, it has been found that the direction of the applied voltage in formation of the ion adsorption preventing structure is desirably adjusted to correspond to the direction of the applied voltage in measurement of the ion current flowing through the nanopore.

Figure 23:
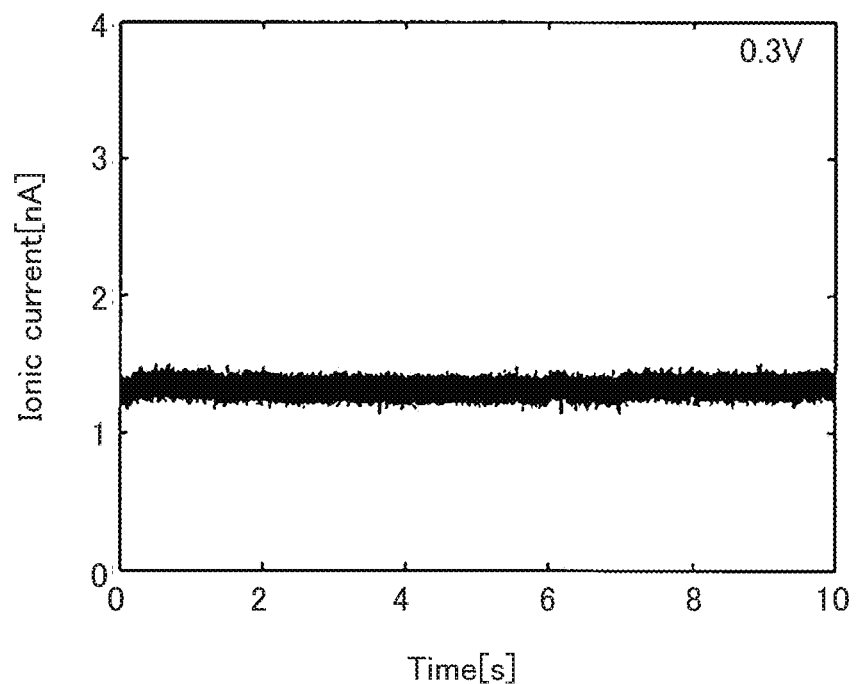
FIG. 23 shows verification results on a noise reduction effect when the first solution is disposed only on one side of a thin film.

FIG. 23 shows verification results on the noise reduction effect when the first solution, one of the two solutions disposed on both sides of the thin film, is disposed only on one side of the thin film. FIG. 23 shows a base current when a nanopore is opened by dielectric breakdown while a first tank is filled with a 1M $CaCl_2$ solution and a second tank is filled with a 1M CsCl solution, and then a 1M CsCl solution is introduced into the solution tank containing the 1M $CaCl_2$ solution and an ion current is measured. As known from the results, it has been found that even if only one tank is filled with the first solution, the cation adsorption preventing structure 8 can be provided by wetting the nanopore wall surface, leading to the RTN reduction effect.

Figure 24:
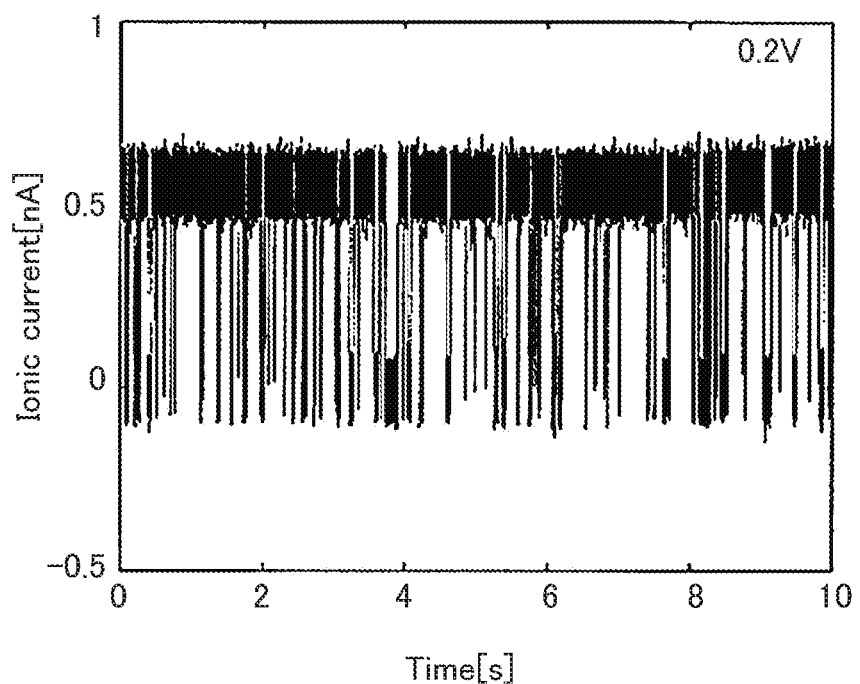
FIG. 24 shows results of measurement of a biopolymer while a cation adsorption preventing structure is provided.

While the first solution was disposed only on one side of the thin film as with the experiment of FIG. 23, and while the direction of the applied voltage in formation of the ion adsorption preventing structure was adjusted to correspond to the direction of the applied voltage in measurement of the ion current flowing through the nanopore as with the experiment of FIG. 22, ssDNA was measured as the biopolymer. FIG. 24 shows results of this experiment. In this experiment, the solution used in opening the nanopore by dielectric breakdown was a 1M $CaCl_2$ solution on the negative side and a 1M CsCl solution on the high-voltage side (+5 to 10 V). After opening the nanopore, a 1M CsCl solution containing DNA was introduced into the solution tank containing the 1M $CaCl_2$ solution (the negative-voltage application side), and +0.2 V was applied to the high-voltage side. At this time, as shown in FIG. 24, since the DNA is negatively charged, it migrates to the high-voltage side and generates a blockage current while flowing through the nanopore. As known from this result, it has been found that only one tank is filled with the first solution, and the direction of the applied voltage in formation of the ion adsorption preventing structure is adjusted to correspond to the direction of the applied voltage in measurement of the ion current flowing through the nanopore, and thus the biopolymer can be measured.

Figure 25:
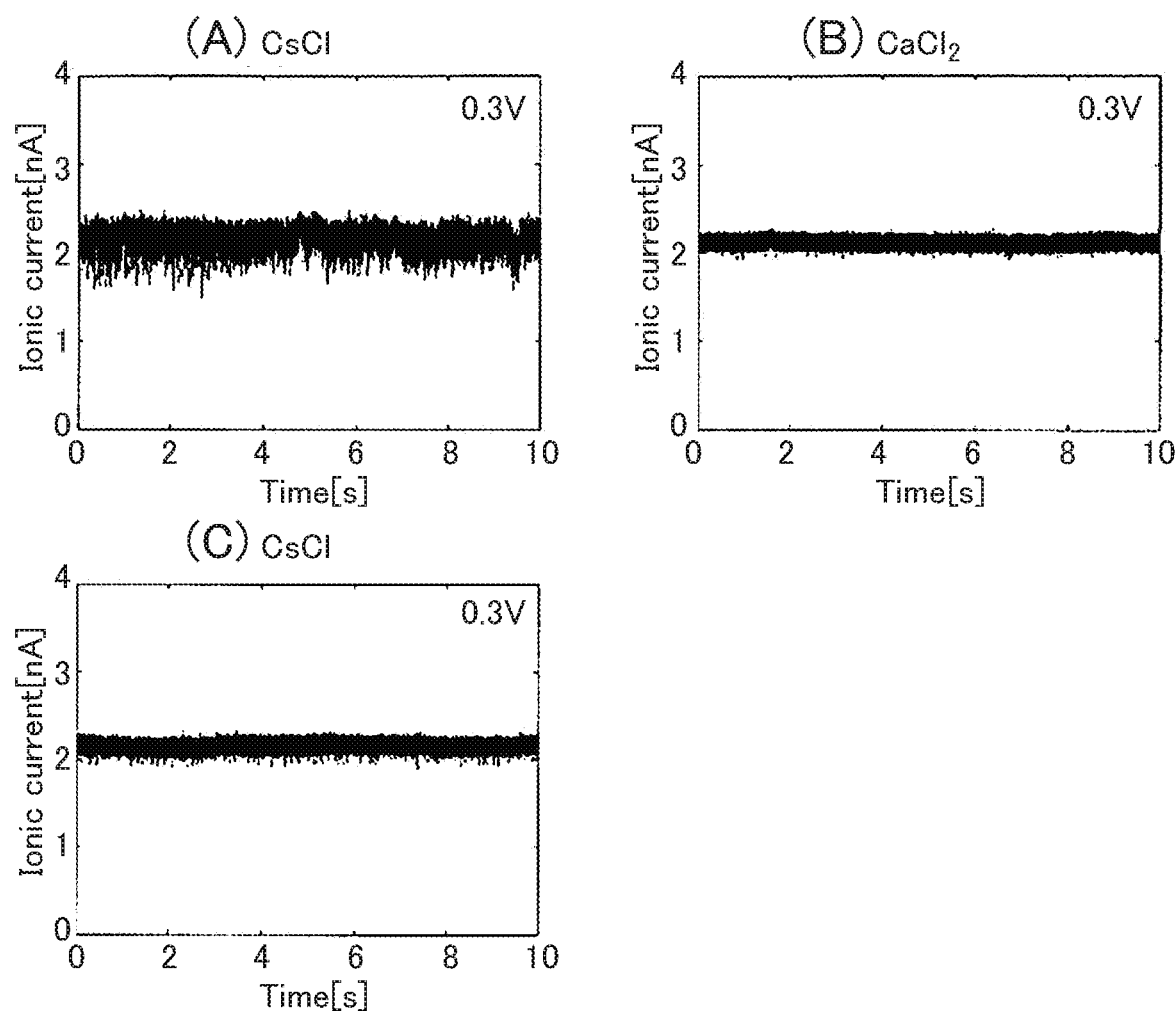
FIG. 25 includes views showing experimental results on a base current when an RTN prevention procedure is performed.
Figure 26:
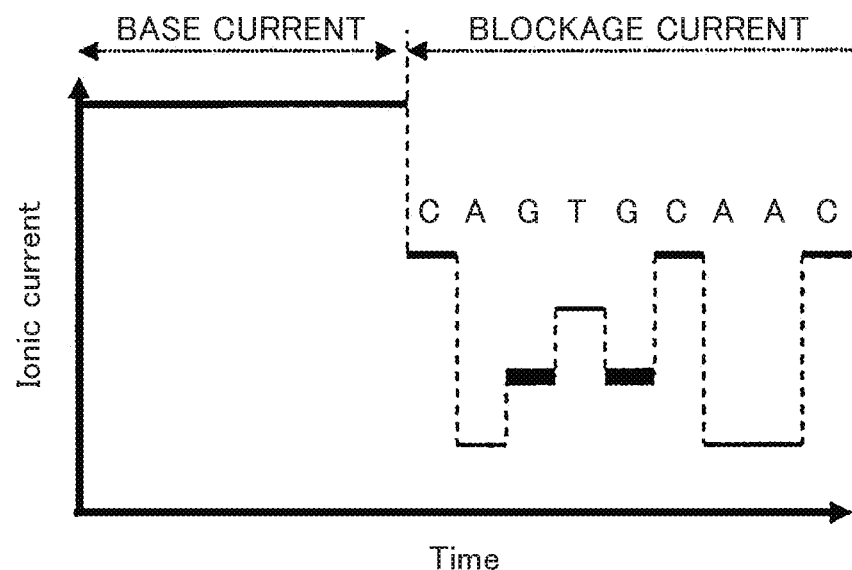
FIG. 26 shows an ideal base current and an ideal blockage current.
Figure 27:
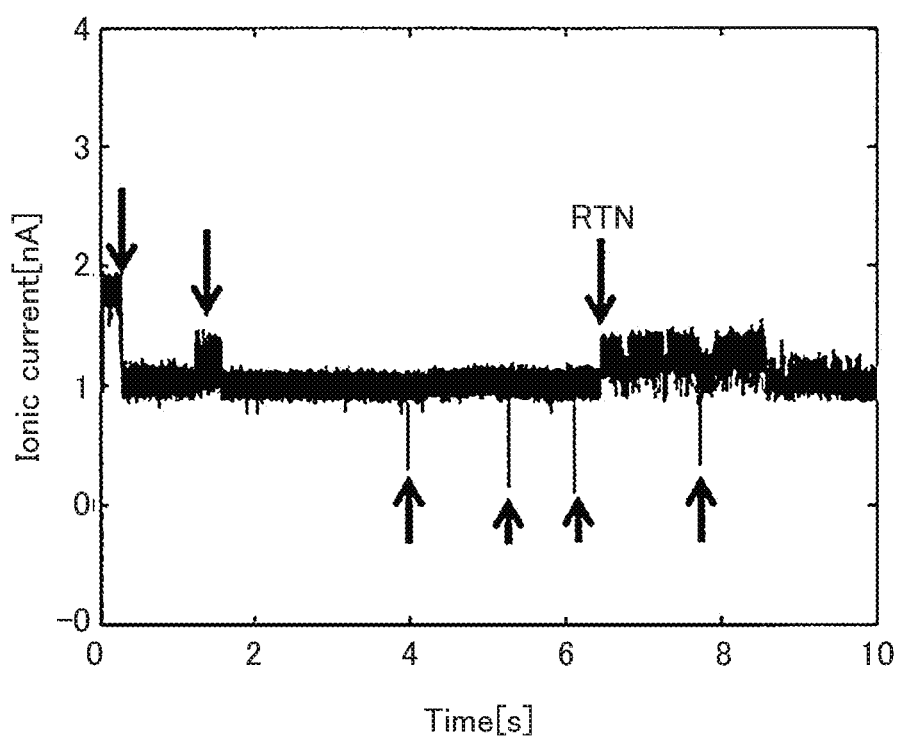
FIG. 27 shows experimental results of abase current having RTN.

In the experiments up to FIG. 24, when the nanopore is formed by dielectric breakdown, the first solution is used so that the ion adsorption preventing structure is formed to suppress RTN. FIG. 25 includes views showing results of suppressing RTN by wetting a previously formed nanopore with the first solution to form the ion adsorption preventing structure. FIG. 25(A) shows a base current when RTN is generated in measurement with a CsCl solution before providing the ion adsorption preventing structure, FIG. 25(B) shows a base current when RTN is suppressed by introducing a $CaCl_2$ solution to form the ion adsorption preventing structure, and FIG. 25(C) shows a base current when RTN is suppressed while the CsCl solution is reintroduced to maintain the ion adsorption preventing structure. As known from such results, it has been found that even if the first solution is introduced to the thin film having no ion adsorption preventing structure, the ion adsorption preventing structure is also formed and RTN can be suppressed.

Although the result of the experiment using the SiN film having a silanol group on the film surface has been shown in each of the above exemplary experiments, the cation desorption/adsorption phenomenon is naturally not limited to the SiN film, and even if a film material is graphene or the like, RTN is also caused by the cation desorption/adsorption phenomenon on a carboxyl group surface or the like, and the present method can be used. The cation adsorption preventing structure is provided by wetting the film surface with the solution in the above exemplary experiments. However, the cation adsorption preventing structure may be formed by a thin film of calcium carbonate, calcium oxide, or calcium silicate, which contains a group II element in the film material or on the film surface. Alternatively, the cation adsorption preventing structure may be formed by precipitating a compound containing a group II element on the surface of a thin film of SiN or $SiO_2$, or by chemically modifying calcium carbonate or the like by mineralization.

The invention is not limited to the above-described examples, and may include various modifications thereof. For example, the examples are described in detail to clearly explain the invention, and the invention is not necessarily limited to inventions having all the described configurations. A configuration of one example may be partially replaced with a configuration of another example. In addition, a configuration of one example may be added to a configuration of another example. Further, a configuration of each example may additionally have part of another configuration, may be partially eliminated, or may be partially replaced with part of another configuration.

LIST OF REFERENCE SIGNS 2 nanopore
3 thin film
8 ion adsorption preventing structure
11 first tank
12 second tank
13 first electrode
14 second electrode
15 power unit
21 first solution
22 second solution
23 third solution
41 partition wall
51 biopolymer
101 fluid controller
105 third tank
106 fourth tank

The invention claimed is:

1. A current measuring method, comprising the steps of:
forming an ion adsorption preventing structure to which a second ion adsorbs to inhibit adsorption of first ions contained in a solution filling a first tank and/or a second tank by wetting a wall surface of a nanopore provided in a thin film with a first solution being a solution containing an ion of a group II element or an acidic solution introduced in at least one of a first tank and a second tank separated by the thin film, the thin film including a material containing Si; and
applying a voltage between a first electrode provided in the first tank and a second electrode provided in the second tank to measure an ion current flowing through the nanopore,
wherein the nanopore is opened through breakdown of the thin film by applying a voltage between the first electrode and the second electrode, and
wherein, when the nanopore is opened, at least one of the first tank and the second tank is filled with an acidic solution as the first solution,
the method further comprising introducing a second solution into the solution tank containing the first solution before measuring the ion current, the second solution having a lower [$H^+$] concentration than the first solution and containing an ion of a group I element, wherein the first solution contains potassium ferricyanide or potassium ferrocyanide.

2. The method according to claim 1, wherein a direction of the voltage that is applied between the first electrode and the second electrode to open the nanopore by breakdown of the thin film corresponds to a direction of the voltage that is applied between the first electrode and the second electrode to measure the current flowing through the nanopore.

3. The method according to claim 1, wherein the group II element is one of Ca, Sr, and Ba.

4. The method according to claim 1, wherein ion concentration of the group II element is 10 mM or more and equal to or less than saturation concentration.

5. The method according to claim 1, further comprising introducing a second solution containing an ion of a group I element into the tank filled with the first solution before measuring the ion current.

6. The method according to claim 5, further comprising applying a voltage between the first electrode and the second electrode before introducing the second solution.

7. The method according to claim 6, wherein a direction of the voltage that is applied between the first electrode and the second electrode before introducing the second solution corresponds to a direction of the voltage that is applied between the first electrode and the second electrode to measure the current flowing through the nanopore.

8. The method according to claim 5, wherein the group I element contained in the second solution is Cs, and ion concentration of Cs is 10 mM or more and equal to or less than saturation concentration.

9. The method according to claim 1, wherein the first solution is introduced into one of the first tank and the second tank, and a third solution containing an ion of a group I element is introduced into the other tank.

10. The method according to claim 9, wherein the group I element contained in the third solution is Cs, and ion concentration of Cs is 10 mM or more and equal to or less than saturation concentration.

11. The method according to claim 1, wherein the concentration of [$H^+$] contained in the first solution is $10^{-5.5}$ M or more and equal to or less than saturation concentration.

12. The method according to claim 1, wherein the concentration of [$H^+$] contained in the second solution is $10^{-14}$ to $10^{-5.5}$ M.

13. The current measuring method according to claim 1, wherein the nanopore has a diameter of 0.1 to 100 nm and a length of 0.1 to 100 nm.

14. The current measuring method according to claim 1, wherein the applying the voltage to measure the ion current includes;
   introducing a biopolymer as an examinee into the first tank or the second tank; and
   measuring a variation in ion current when the biopolymer passes through the nanopore.

* * * * *